(12) United States Patent
Dahan et al.

(10) Patent No.: US 11,772,952 B2
(45) Date of Patent: Oct. 3, 2023

(54) WATER-BASED LIQUID SUPPLY SYSTEM

(71) Applicant: Unito Smart Technologies Limited, Hong Kong (HK)

(72) Inventors: Yuval-Yoni Dahan, Rishon LeTzion (IL); Abraham Dahan, Rishon LeTzion (IL)

(73) Assignee: UNITO SMART TECHNOLOGIES LIMITED, Tsuen Wan NT (HK)

(*) Notice: Subject to any disclaimer, the term of this patent is extended or adjusted under 35 U.S.C. 154(b) by 1156 days.

(21) Appl. No.: 16/291,110

(22) Filed: Mar. 4, 2019

(65) Prior Publication Data

US 2019/0270630 A1 Sep. 5, 2019

(30) Foreign Application Priority Data

Mar. 2, 2018 (EP) .................................... 18159765
Mar. 5, 2018 (EP) .................................... 18159914

(51) Int. Cl.
*A23L 2/54* (2006.01)
*A61L 2/10* (2006.01)
(Continued)

(52) U.S. Cl.
CPC .................. *B67D 1/12* (2013.01); *A23L 2/54* (2013.01); *A61L 2/10* (2013.01); *B01F 23/236* (2022.01);
(Continued)

(58) Field of Classification Search
CPC .......... C02F 1/325; C02F 1/003; C02F 1/008; C02F 1/68; C02F 2209/42; C02F 2303/04;
(Continued)

(56) References Cited

U.S. PATENT DOCUMENTS 4,615,466 A * 10/1986 Credle, Jr. ........... B67D 3/0019
  137/240
4,903,862 A * 2/1990 Shannon .............. B67D 1/1252
  222/206
(Continued)

FOREIGN PATENT DOCUMENTS

WO 2016040986 A1 3/2016
WO 2016172037 A2 10/2016

OTHER PUBLICATIONS

European Application No. EP18159914.3, Extended European Search Report, dated Oct. 14, 2019, 16 pages.
(Continued)

*Primary Examiner* — Eric S Stapleton
(74) *Attorney, Agent, or Firm* — Kilpatrick Townsend & Stockton LLP

(57) ABSTRACT

Kitchen appliances usually include devices such as a water system, a cooker, a kitchen hood (range hood), an oven, a refrigerator, a microwave, a dishwasher and other devices. The devices are mostly operated independent from each other. Unlike those devices the "drinkable tap water-based liquid supply system" according to the present invention comprises a few devices controlled by an advanced control system according to the invention for providing connectivity and system management. The system is designed to provide comfort, convenience and energy saving. The water-based liquid supply system according to the present invention provides a variety of water-based liquids, dispatched with the desired properties from a countertop faucet.

53 Claims, 14 Drawing Sheets

(51) Int. Cl.
- *B67D 1/04* (2006.01)
- *B67D 1/08* (2006.01)
- *C02F 1/00* (2023.01)
- *B67D 1/12* (2006.01)
- *C02F 1/68* (2023.01)
- *C02F 1/32* (2023.01)
- *G01F 23/24* (2006.01)
- *B01F 23/236* (2022.01)
- *B01F 23/237* (2022.01)

(52) U.S. Cl.
CPC ......... *B67D 1/0406* (2013.01); *B67D 1/0857* (2013.01); *C02F 1/003* (2013.01); *C02F 1/008* (2013.01); *C02F 1/325* (2013.01); *C02F 1/68* (2013.01); *G01F 23/241* (2013.01); *A23V 2002/00* (2013.01); *A61L 2202/11* (2013.01); *A61L 2202/14* (2013.01); *B01F 23/2364* (2022.01); *B01F 23/237621* (2022.01); *C02F 2209/42* (2013.01); *C02F 2303/04* (2013.01)

(58) Field of Classification Search
CPC ........... E03C 1/057; E03C 1/044; E03C 1/02; E03C 1/0404; E03C 2201/45; E03C 2201/40; B67D 1/0022; B67D 1/0406; B67D 1/0059; B67D 1/12; B67D 1/0857; A23L 2/54; G01F 23/241; B01F 23/236; B01F 23/237621; B01F 23/2364; A61L 2/10; A61L 2202/11; A61L 2202/14; A23V 2002/00
USPC ....................................................... 99/323.2
See application file for complete search history.

(56) References Cited

U.S. PATENT DOCUMENTS

| | | | | |
|---|---|---|---|---|
| 4,909,047 | A * | 3/1990 | Koeneman | B67D 1/0857 222/318 |
| 5,000,357 | A * | 3/1991 | Shannon | B67D 1/0051 239/406 |
| 5,033,645 | A * | 7/1991 | Shannon | B67D 1/1252 222/61 |
| 5,417,348 | A * | 5/1995 | Perrin | F16K 19/006 4/675 |
| 5,592,867 | A * | 1/1997 | Walsh | B67D 1/0057 261/DIG. 7 |
| 5,706,661 | A | 1/1998 | Frank | |
| 6,182,949 | B1 * | 2/2001 | Mobbs | B67D 1/0068 261/DIG. 7 |
| 7,861,544 | B2 * | 1/2011 | Ferreira | B67D 1/0057 62/272 |
| 2002/0046569 | A1 * | 4/2002 | Faqih | B01D 5/009 62/93 |
| 2012/0035761 | A1 * | 2/2012 | Tilton | B67D 1/0057 700/239 |
| 2013/0062366 | A1 * | 3/2013 | Tansey | B67D 1/0809 222/101 |
| 2014/0030383 | A1 * | 1/2014 | Marchetti | B67D 1/0406 99/323.1 |
| 2015/0053626 | A1 * | 2/2015 | Caulkins | C02F 1/34 210/178 |
| 2015/0329346 | A1 * | 11/2015 | Miller | B67D 1/0884 222/23 |
| 2017/0055761 | A1 * | 3/2017 | Roberts | A47J 31/407 |
| 2017/0360243 | A1 * | 12/2017 | Crowne | A23L 2/54 |

OTHER PUBLICATIONS

European Application No. EP18159914.3, Office Action, dated Jun. 29, 2021, 5 pages.

European Application No. EP20190219.4, Extended European Search Report, dated Nov. 27, 2020, 8 pages.

* cited by examiner

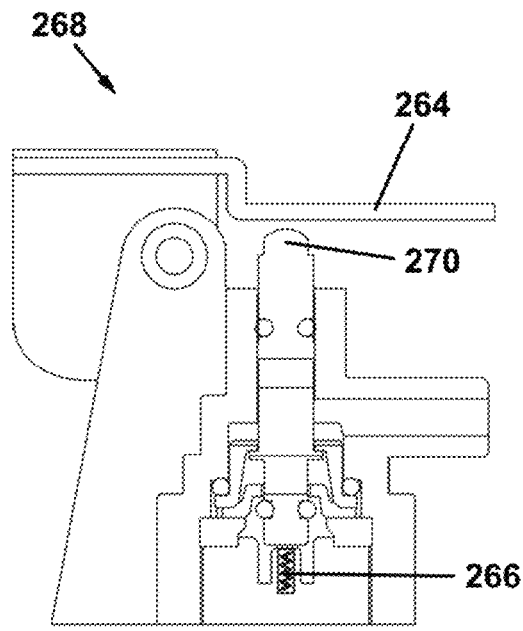 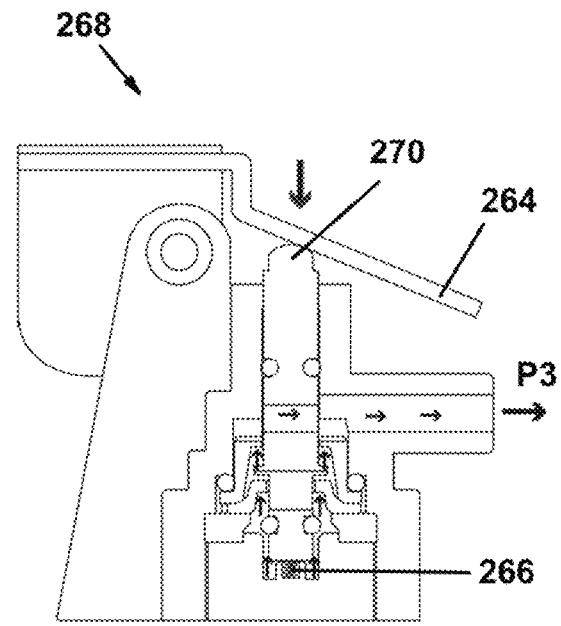
Fig. 8A  Fig. 8B
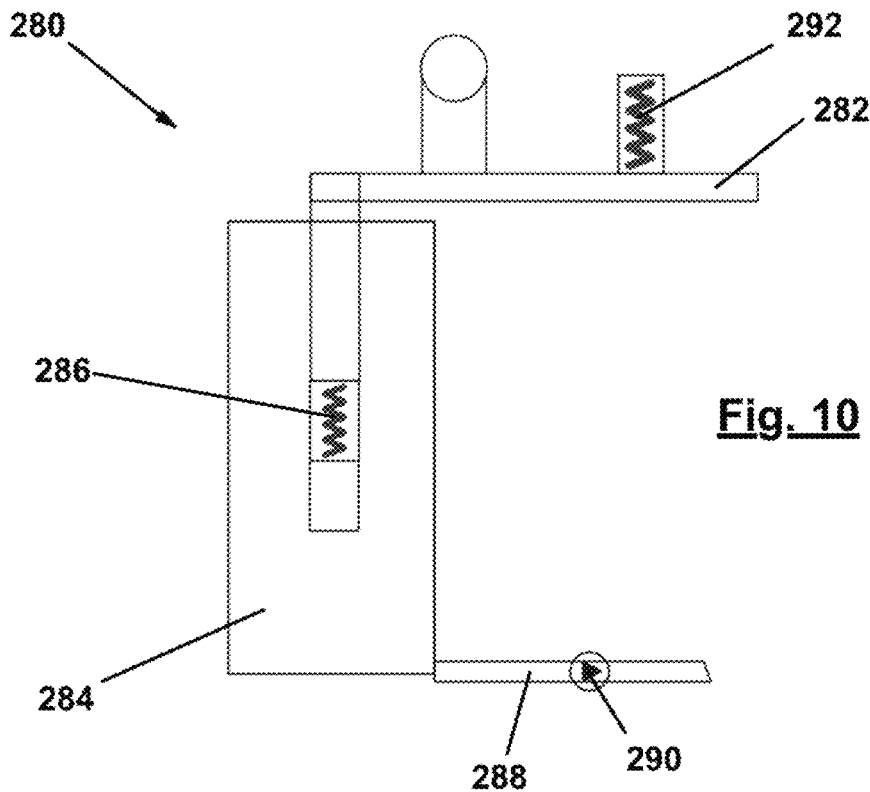
Fig. 10

WATER-BASED LIQUID SUPPLY SYSTEM

CROSS REFERENCE TO RELATED APPLICATION

This application claims priority to European Patent Application No. 18 159 765.9, filed in Europe on Mar. 2, 2018, and European Patent Application No. 18 159 914.3, filed in Europe on Mar. 5, 2018, the entire contents of each which are hereby incorporated herein by this reference.

FIELD OF THE INVENTION

The present invention relates to a water-based liquid supply system, preferably a drinkable tap water-based liquid supply system, including a controlling system, possibly integrated in a kitchen environment, and possibly connected in-house to other smart appliances as well as to the outside world. The connectivity is built on few layers for indoor and outdoor connectivity and control.

BACKGROUND OF THE INVENTION

The water-based liquid supply system disclosed comprises the following components:
  a water-based liquid supply system concept containing one or more elements such as
  a faucet,
  a carbonation machine (soda machine),
  a boiler for supplying hot and/or boiling water,
  a liquid level sensor (for the soda machine),
  a water system manifold,
  a water sterilizing unit, e.g. if the water hasn't drinking water quality (which, for example, can happen if the water is kept for a long time in a tank),
  a water enrichment system (flavor system),
  an intelligent wired and/or wireless control system managing and controlling all these components.

1 The Water-Based Liquid Supply System 1.1 Prior Art There are many water supply systems for kitchen existing in the market. Some of these systems are offering instant hot water, some instant chilled water or soda. Some include water purifying elements, some don't. The known systems operate individually, i.e. isolated from each other devices, with an attached control unit controlling the operation and the parameter set up. The known systems are installed either on the countertop or under the sink and most of them are not flexible for change (expansion thereof) after installation.

1.2 Invention The system according to the present invention provides a new concept of a "water-based liquid supply system" operating as one single unit both, internally, i.e. on its own, and externally with other smart appliances, e.g. other smart kitchen appliances, supported by a communication and control platform, controlling operation, set ups and connectivity with smart device application, flexible for expansion, and highly efficient.

The present invention relates to water-based liquid supply system, in particular for under-sink installation, for dispatching one or more water-based liquid(s) such as hot water, chilled water and carbonated water (soda), hot and cold beverages carbonated or non-carbonated from at least one countertop faucet, backed by a sophisticated control system platform that works at a few complexity levels, providing indoor and outdoor connectivity to the system. The indoor connectivity interconnects the system devices as well as connects the system devices to smart devices application(s) suitable for smartphone, tablet or alike. The system may be connected to the internet for outdoor connectivity.

2 The Faucet 2.1 Prior Art Most faucets are designed to dispatch hot or cold or mixed water. They have an inlet for cold water and an inlet for hot water. The basic faucet design includes a faucet base connected countertop having one or more supply pipes connected thereto as well as valves for controlling the water outlet, a spout, usually a rotating spout, connected to the base, and an aerator to shape the dispatched liquid.

2.2 Invention The present invention relates to a "multiple liquid flow faucet" with a base element and a pivoting spout, comprising at least one connection to the main water line and one or more connections to the water-based liquid supply. The water-based liquid is dispatched by operating an electronic knob or a mechanical knob to select the type of liquid required and dispatch it through the spout by opening the selected mechanical valve or solenoid valve.

The water-based liquid supply may contain liquids at different temperatures, different tastes and different concentrations. This requires separation of the passages from the supply storage to the outlet, while the passages are thermally isolated from the faucet elements, i.e. separating at a first level the drinking water-based supply from the non-drinking water, e.g. used for dishing and washing, and at a second level separating the various types of drinking water-based liquids from each other.

It is therefore an object of the present invention to solve the problems arising from the prior art, and in particular to specify a multiple flow faucet with a rotatable pivoting spout.

3 The Carbonation Machine (Soda Machine)

3.1 Prior Art Different carbonation machines, also called soda machines, are designed to provide carbonated water, also called soda or sparkling water, on demand combined with or without chilled water. Some of them are designed to prepare and dispatch a limited quantity of soda suitable to fill a cup or a bottle. Others are designed to prepare the soda in a removable container, or to prepare the soda continually by injecting water and $CO_2$ simultaneously into the carbonation tank. Typically, such systems comprise a high-pressure carbonation tank with gas communication to a carbon dioxide ($CO_2$) cylinder through a pressure regulator in which the pressure to be supplied to the carbonation tank is reduced from approximately 60 bar (at about 22° C.) to approximately 5 to 10 bar. Furthermore, such communication between the $CO_2$ cylinder and the carbonation tank utilizes an on/off valve to open and close the pipe communications between the $CO_2$ cylinder and the carbonation tank for controlling the supply of the $CO_2$.

Many other soda systems require a motorized pump to pressurize the water supplied to the $CO_2$ tank to high pressure to overcome the pressure of the $CO_2$ gas contained therein or to increase the mixing process efficiency.

The soda machines are further divided into countertop machines and under-sink machines that are designed to fit specific requirements such as minimum size and low noise.

It is known that water must be cooled to a low temperature prior the carbonation process to achieve higher absorption of $CO_2$ gas into the water. Moreover, in order to further increase the absorption of the $CO_2$ gas, a certain pressure level must be controlled in the tank during the mixing process and later on to keep the $CO_2$ from diffusing. For under-sink water systems, it is further required to dispatch the carbonated water while keeping a smooth flow and preventing it from heating on the way out. Otherwise the absorbed $CO_2$ can easily be diffused from the soda water.

Moreover, the soda dispatched usually mixes with any liquid present in the pipes and may be affected.

U.S. 2015/0037464 A1 discloses systems and methods for providing carbonated water through a typical kitchen faucet. The faucet-integrated carbonation system includes a carbonated water reservoir coupled to a residential or commercial cold-water supply line as well as a $CO_2$ tank, all of which can be mounted under a kitchen countertop or the like. The water held in the reservoir can be carbonated using the $CO_2$ when a user activates a $CO_2$ activation mechanism. The system can further include a carbonated water on/off valve for dispensing carbonated water from the carbonated water reservoir via a waterway with an outlet disposed at the end of the faucet.

U.S. 2015/0024088 A1 describes a system and method for providing different levels of carbonated water on demand. The system includes a pressurized chamber to hold at least one of water and carbonated water, a gas canister to dispense carbon dioxide ($CO_2$) regulated by a pressure regulator into the pressurized chamber via a controlled valve, a controller to control the dispensing of the $CO_2$ according to level of carbonation required and a valve to vent excess gas from the pressurized chamber after carbonation EP 2 861 521 A2 proposes the use of a valve to inject $CO_2$ at regulated pressure, and then reduce the pressure in the carbonation tank before dispatching the beverage. It further comprises a water separator for separating the water drops released together with the gas.

U.S. Pat. No. 9,409,759 relates to a machine for preparing and dispatching either carbonated or non-carbonated beverage at predefined quantity. It presents a similar process for a soda producing method as described in EP 2 861 521 A2.

U.S. Pat. No. 6,216,913 describes a process of preparing carbonated water by injecting $CO_2$ gas to fill the carbonating tank and then inject water at high pressure into the tank using a pump.

WO 2014/037456 A1 describes a water dispensing machine comprising a water container which is connected by pump means to a carbonation container adapted to receive a quantity of water from said water container, and a gas container, which is connected to said carbonation container for dispensing gas into the quantity of water contained in said carbonation container via a magnetic valve that controls the $CO_2$ injection, said carbonation container being connected to a dispensing device for dispensing said quantity of water into an external container adapted to be accommodated at said dispensing device.

3.2 Invention The proposed invented soda machine offers a new construction, new components, and a new processing cycle utilizing non-regulated, very high-pressure injection of $CO_2$ gas (about 60 bar at about 22° C.) with new protection securing methods to protect the system from failure, and provide high quality soda, suitable for personal preferences.

The soda machine according to the present invention presents a different process of soda preparation and dispatching for use. The chilled water container is different and connected to the soda container. The soda machine according to the present invention presents methods of preparing soda, which are different from that of the known soda machine.

4 The Liquid Level Sensor (Used for the Carbonation Machine)

4.1 Prior Art Different liquid level sensors are known in the market. Some of them propose sensing the liquid level by using two electrodes, which sense the change of the resistance when fluid fills the gap between them or by measuring the resonance or capacitance, which changes when water or liquid fills the gap between the electrodes. Other known liquid level sensors offer sensing the liquid level by using a floating device that changes height together with the liquid level or optical sensors that sense the water level optically. A few solutions are offered based on piezoelectric devices by detecting the change of resonance of the piezo device when liquid is detected.

U.S. 2003/0010117 A2 discloses a water level sensor which includes a reference electrode comprised of a plurality of electrode plates to detect the electric conductivity of the water filling a space between the electrode plates of the reference electrode.

JP 2011-215144 A proposes to detect the electrostatic change between two electrodes with peripheries to measures the capacitance between the electrodes.

JP H10-300559 proposes to detect the float movement up and down.

JP S63-196821 proposes on the basis of the magnitude of the change of the frequency when there is water at the part of the water level sensor.

EP 0 745 833 A1 proposes a liquid level sensor comprising a piezoelectric receiver having two complementary active area segments for capturing ultrasonic signals emitted from a piezoelectric transmitter.

4.2 Invention The present invention proposes sensing the liquid level by using a sensor which is based on grounded water (possible by grounding the metal tank) and conductive liquid (e.g. drinking water).

The liquid level sensor according to the present invention uses a charged sensor electrode, the electrical characteristics of which changes when liquid touches the sensor.

5 The Water System Manifold 5.1 Prior Art Many manifolds exist in the market. Most of them are basically related to a pipe or chamber branching into several openings.

5.2 Invention The present invention relates to a flexibly expendable manifold receiving liquid from a few sources and distributing it to the faucet or to drain. The manifold includes functional elements, such as solenoid valves, check valves, sensors, safety components such as a pressure relief valve and a safety group, and consumable items such as at least one water filter, at least one $CO_2$ canister or cylinder, at least one UV light source, at least one syrup can etc. The proposed manifold complies with multiple functions required from the flexible (expendable) system distributing a variety of liquid types.

6 The Water Sterilizing Unit 6.1 Prior Art

Many types of UV light water sterilizing units are used in water systems to make them inhospitable environments to microorganisms, such as bacteria, viruses, molds and other pathogens. Most of these UV light units are positioned a tank where water is stored before use.

6.2 Invention The sterilizer according to the present invention comprises an ultraviolet (UV) disinfection system and uses a method for treating fluids, in particular purified drinking water, with at least one UV light source or lamp that is either positioned inside a water pipe or outside a transparent water pipe. When the UV light source is positioned inside the water pipe or conduit, the UV light is projected into the surrounding water while flowing towards the faucet. When the UV light source is positioned outside the conduit (along the fluid pipe), the UV light source projects the light into the transparent pipe and the fluid to be treated, while flowing along the UV light source.

7 The Water Enrichment System (Flavor System)

7.1 Prior Art

According to the prior art, additives may be added either by including an additive device with a reservoir and a mixing chamber for receiving a fixed amount of flavor additive allowing providing the mixture of the flavor additive and water. Some systems may use the option of a mixing capsule of fixed amount of additive to be mixed in the water or soda.

7.2 Invention The water-based liquid supply system according to the present invention includes the option of an enrichment device enriching the water-based supply with a variety of optional, e.g. liquid-based, additives such as flavor, taste, tea, coffee, vitamins, minerals etc. The system may comprise one or more tanks, preferably consumable tanks, containing the additives selection, a precise pump, a pipe connecting the respective tank to the system pipe in communication with the faucet. The pump may be controlled by the system control or alternatively directly operated by a user to dispatch the enrichment required at a controlled amount whenever desired. The system may further include a mechanism to prevent an uncontrolled flow of material.

8 The Control System 8.1 Prior Art There are many control systems and many applications in the market. Some are specifically designed to control any home appliances (IOT—internet of things) as well as to remotely activate home units. Many applications offer limited remote power on/off activation for a boiler or an air-conditioning device or other devices, others offer the option to monitor the appliances with a camera, for example to remotely view the house or the devices, such as the refrigerator or oven contents.

U.S. 2014/0129006 A1 discloses a smart controlling method applied to a smart home system for controlling a number of home appliances which may be activated upon detection that a user is approaching the smart home.

WO 2016/058367 A1 discloses a smart home control system comprising a home control center and a control terminal that can exchange data. A smart home control module and a router module within the home control center can exchange data with each other, and smart home appliances can exchange data with the router module.

WO 2016/172037 A2 discloses a control unit specifically for under-sink kitchen appliances. The control unit is located under a kitchen sink. The control unit controls the timing of the power demand from each device and accommodates sensors and other accessories. The communication is performed either wired or wireless.

8.2 Invention The present invention discloses an apparatus and a method for operating and controlling a variety of smart kitchen devices operated by an upgradable "smart control unit". The system may operate in a few optional modes indoor and/or outdoors, e.g. connected to a cloud and possibly supported by other applications.

SUMMARY OF THE INVENTION

Summarizing, the present invention relates to a liquid supply system for preparing and dispensing water-based liquids at a desired temperature and/or with at least one additive at a desired concentration on demand, the liquid supply system comprising a water supply comprising at least one water tank and/or a connection to a water main line, at least one faucet having an outlet for dispensing the prepared water-based liquid, and at least three of the following additional devices a water filter adapted to filter water from the water supply, a water boiler adapted to heat water from the water supply to a predetermined temperature, a water chiller adapted to cool water from the water supply to a predetermined temperature, a soda machine adapted to carbonize water from the water supply to a predetermined $CO_2$ concentration, and an additive mixer adapted to mix at least one additive supplied from at least one additive container at a predetermined concentration to water from the water supply, the liquid supply system further comprising a piping system connecting the water supply, the faucet and the at least three additional devices installed in the liquid supply system, and a communication and control system adapted to communicate with a user and to control the preparation and dispensing of the water-based liquid based on a communication with the user.

The liquid supply system can be adapted to prepare and dispense a wide range of different water based liquids such as water at different temperatures from chilled water, or even ice cubes, to boiling water, differently flavored hot and cold beverages, either carbonated or not, soft drinks, coffee, tea, soup and so on. In particular, the water based liquid supply system can be adapted to prepare and dispense a drink on demand at a desired temperature and/or a desired degree of carbonization and/or a desired concentration of an additive or additives, such as flavors, minerals or vitamins. Those additives can be stored in the system in any convenient form, e.g. as liquid and/or powder and/or pill etc.

Preferably, the faucet is a counter-top faucet with an over-sink outlet and several or most of the other components of the liquid supply system except an optional user interface of the communication and control system are under sink components.

In order to prepare special types of liquids, suitable machines, in particular under-sink machines can be provided in the liquid supply system according to a preferred embodiment of the invention.

The additive mixer preferably comprises at least one pump for supplying a predetermined additive or several additives, such as flavors and/or minerals and/or vitamins at a predetermined concentration from the respective additive container to water from the water supply.

Furthermore, at least a part of the piping system may be adapted to be drained and/or to be flushed with a cleaning liquid, preferably boiling water, regularly or on demand or at predetermined occasions, such as a change in the kind of water-based liquid selected by the user.

According to a preferred embodiment, the piping system comprises a manifold for handling and distributing liquid and/or gas flow in particular for combining liquids from different sources.

Preferably, at least the manifold and those pipes of the piping system connecting the manifold to the faucet are adapted to be drained and/or flushed with a cleaning liquid in order to avoid a contamination of a currently desired kind of water-based liquid with rests of a previously prepared other kind of water-based liquid.

It is also possible to flush the afore-mentioned part of the piping system for example with cold water after dispensing a hot liquid in order to cool down the piping system so that a cold drink ordered after a hot drink is not unintentionally heated by the piping system.

For hygienic reasons, the liquid supply system preferably comprises at least disinfection device, in particular at least one UV sterilizer adapted to sterilize a liquid in a tank or flowing through a pipe by irradiating it with UV light, e.g. between the manifold and the faucet or between a tank and the manifold. Corresponding UV lamps or UV sources can be provided either inside or outside a tank or pipe. In the latter case it is preferred that the tank or pipe is at least locally transparent. The liquid supply system is preferably adapted to control the UV sterilizer in such a manner that the UV source is only turned on when necessary.

As an alternative, the liquid supply system can be adapted to regularly flush at least one liquid container, preferably all liquid containers, and most preferably also the piping system with boiling water from the water boiler.

Furthermore, several components of the liquid supply system, such as the faucet, the water supply, one or several of the additional devices installed in the liquid supply system, the piping system or parts of the piping system, may be smart appliances adapted to communicate with each other and/or with the user and/or the outside world via the communication and control system, wherein the communication and control system may be adapted to be accessed by the user via a local, proprietary control panel and/or via a mobile device such as a smartphone or tablet computer with a suitable mobile app, and wherein the communication and control system may be adapted to be accessed by the user directly and/or via a local hub or via cloud communication through the internet.

Furthermore, the communication and control system may be adapted to monitor the consumption of at least one consumable part of the system such as a water filter and is preferably furthermore adapted to calculate an expected service life of the at least one consumable part taking into consideration the monitored consumption, and preferably at least one other influencing parameter, such as water quality, in particular water hardness, and/or ambient temperature.

Preferably, data, such as the hardness of water at the specific geographical place of the system can be taken into consideration. These data can be inserted into the system either manually by the user or by connecting the system to the internet and retrieving the data from a suitable web site. The consumption of a water filter as a consumable part can, for example, be monitored by monitoring the quantity of water passing through the filter and by taking the hardness of the water at the current position of the system into consideration.

According to a preferred embodiment, the system comprises components, such as tanks or machines, that require operation parameters, e.g. for temperature or concentration control, and the parameter setting can be provided remotely or on demand, optionally taking into consideration additional data, such as the ambient temperature, seasonal conditions, geographic location, climate etc. As explained above, those additional data can be inserted manually or can be retrieved via the internet. Alternatively, the parameter setting can by defined by a suitable algorithm.

Advantageously the communication and control system may adapted to recognize and react to user voice commands. Preferably, the liquid supply system is connectable or connected to an internal audio assistance provider, such as "Tiana", the applicant's internally developed microphone with supporting software that translates voice commands to action. "Tiana" is similar to "amazon echo" and "google home". But while these two external services were developed to fit many applications, Tiana was specifically developed to support the applicant's systems. However, it is also conceivable to adapt the water-based liquid supply system to an external third party audio system, such as "google home" or "amazon echo".

Furthermore, according to a preferred embodiment, the voice commands which may be recognized by the communication and control system comprise, in addition to on/off-commands, at least one further command regarding the desired quantity of the liquid to be dispensed and/or the desired type of liquid (e.g. water, soda, coffee, . . . ) and/or the desired temperature and/or the desired type of additive, e.g. flavor, and/or the desired additive concentration. In short, it is preferred that the user can order his or her desired drink with detailed specifications by voice command.

Furthermore, the liquid supply system may comprise an expandable manifold having at least one exchangeable board, each board comprising at least one ingoing pipe, preferably a plurality of ingoing pipes, and at least one outgoing pipe, preferably a plurality of outgoing pipes.

According to a preferred embodiment, the manifold for handling and distributing liquid and gas flow is expandable, i.e. at least one further exchangeable board may be added to the manifold. In order to allow for easy expandability, the manifold can comprise at least one exchangeable board. In particular, the manifold can comprise a plurality of slots or mounting positions for exchangeable boards.

Furthermore, the manifold may optionally comprise or be connected to consumable parts, such as a $CO_2$-cylinder and/or a water filter and/or at least one water flavor device and/or at least one disinfection device. Several or all of those consumable parts can optionally be mounted on the exchangeable board(s).

Furthermore, the liquid supply system may comprise a water tank connected to the water main line and adapted to store water at a predetermined temperature, wherein the liquid supply system is adapted to calculate a temperature of water in the water main line based on a quantity of water stored at the predetermined temperature in the water tank at a given time, a quantity of line water additionally filled into the tank and the resulting temperature difference of the water in the water tank.

For example, the water tank can be a water boiler, wherein the temperature of water in the main line is calculated from the temperature drop resulting from filling a defined quantity of water from the main line to a known quantity of boiling water in the boiler.

The water tank can also be a water chiller, wherein the temperature of water in the main line is calculated from the temperature rise resulting from filling a defined quantity of water from the main line to a known quantity of chilled water in the water chiller.

Furthermore in order to provide water at a desired temperature, the system can be adapted to mix water from at least two water tanks storing water at different temperatures in suitable proportions.

According to a further embodiment, the faucet may comprise at least two internal conduits, preferably coaxial internal conduits, the internal conduits being separated, and preferably also thermally insulated, from each other. This is especially advantageous when the water main line carries water that is not suitable for drinking without further measures such as filtering and/or sterilizing and/or boiling. In this manner, drinkable liquids can be safely separated from the non-purified main line water.

Preferably, the faucet comprises at least two coaxial conduits. Therein, the inner conduit can for example be adapted to carry drinkable liquids, whereas the outer conduit can be adapted to carry water from the water main line for other purposes than drinking, e.g. washing and dishing.

According to a further preferred embodiment, the inner conduit can be divided into at least two separate ducts adapted to carry different kinds of drinkable liquids in order to avoid any cross contamination, the at least two separate ducts being optionally also thermally insulated from each other, preferably from the entry point to the outlet of the faucet. These at least two separate ducts can preferably also be provided coaxially to each other and more preferably still also to the outer conduit.

Providing separate conduits or ducts that are arranged coaxially is especially advantageous for a faucet with a swiveling spout. In particular, the cross section of each of the separate coaxially arranged conduits or ducts can be circular at least in the end region in which the swiveling spout is connected to a fixed part of the faucet. With this arrangement, the spout can be swiveled without putting a strain on the internal conduits.

However, as an alternative, a flexible pipe, preferably a flexible pipe for each internal conduit or duct can be inserted in the spout or part of it in order to connect the internal conduit or duct in the spout with a pipe, conduit or duct extending in the faucet base, the flexible pipe being suitable to being twisted in order to prevent damage when the spout is swiveled.

Furthermore, the liquid supply system may be adapted to prepare a predetermined number of different kinds of water-based liquids, each of these different kinds of water-based liquids being associated with a specific predetermined indication, e.g. with a specific predetermined color, and wherein the liquid supply system, preferably the faucet, comprises a display device adapted to display the specific predetermined indication associated with the kind of water-based liquid that is currently being selected, prepared or dispensed.

Here, different kinds of water-based liquids are water-based liquids which are different from each other in at least one of the following qualities: temperature or temperature range, type of additive and additive concentration or concentration range, in particular $CO_2$ concentration.

Preferably, the system may also comprise a selector device that is mechanically adjustable, preferably rotatable, in predefined steps between different positions in order to select one of the predetermined number of different kinds of water-based liquids. Furthermore, the system can comprise a detector device for detecting the current position of the selector device.

Furthermore, the liquid supply system may comprise a selector knob for selecting the desired kind of water-based liquid, the selector knob comprising an outer shell being adapted for, preferably bidirectional, rotation around an axis in predefined steps with respect to a fixed part, e.g. of the faucet, a reflecting element provided on one part, namely the outer shell or the fixed part, an illuminating element provided on the respective other part, namely the fixed part or the outer shell, and adapted to illuminate the reflecting element, and an optical sensor device provided on the respective other part, and adapted to detect the intensity of light reflected from the reflecting element so that a rotation of the outer shell by one step is detected by a change of the intensity of light reflected from the reflecting element.

The reflecting element may be a reflector ring or a reflector disk divided in n sectors of equal form and size having alternatingly high and low reflectivity, n being a natural even number, and each sector covering an circumferential angle of 360°/n around the axis, and wherein the sensor device comprises two sensor elements arranged in a circumferential distance of 180°/n.

In this manner, the rotational direction and the current position of the selector knob may be detected. Furthermore, as not the change in reflectivity is detected but the reflectivity is detected after a one step rotation of the selector knob has been completed, slower sensors can be used.

Furthermore, the liquid supply system may comprise a soda machine adapted to carbonize water from the water supply to a predetermined $CO_2$ concentration, the soda machine comprising a $CO_2$ container containing $CO_2$ at a CO2 container pressure, e.g. a pressure of 60 bar at about 22° C., a soda tank connected to the water supply and to the $CO_2$ container, the connection between the $CO_2$ container and the soda tank being free of a pressure reducer or valve, a $CO_2$ release mechanism for releasing and injecting $CO_2$ gas from the $CO_2$ container directly into the soda tank through a nozzle located in the soda tank, and a check valve installed in the line connecting the $CO_2$ container and the soda tank and preventing $CO_2$ gas or soda water from flowing back from the soda tank to the $CO_2$ container.

Releasing and injecting the non-regulated $CO_2$ gas from the container at high pressure directly through the nozzle into the soda tank results in turbulence thus achieving an efficient mixing of the $CO_2$ gas in the water. The check valve keeps the pressure in the soda tank high and prevents leakage of gas or soda water when the $CO_2$ container is disconnected, e.g. for replacement purposes.

The water supply may comprise a separate tank for storing chilled water, the soda tank in one embodiment being partially submerged in the separate tank, and wherein the soda tank and the separate water supply tank may each be provided with cooling coils for direct cooling.

Furthermore, the soda machine may comprise an auxiliary $CO_2$ circulation system comprising an expansion tank, a pipe connecting the expansion tank to the soda tank via a pressure relief valve that opens when the pressure in the soda tank and the pipe exceeds a preset pressure and a further pipe connecting the expansion tank to the soda tank via a one-directional valve blocking a flow of $CO_2$ gas and water or water droplets from the soda tank to the expansion tank.

Furthermore, the $CO_2$ release mechanism may comprise a gap reducing mechanism adapted to reduce a backlash between components of the $CO_2$ release mechanism and the $CO_2$ container due to accumulated engineering tolerances of these components and/or due to changes in the mounting position of the $CO_2$ container when the $CO_2$ container is exchanged.

Furthermore, the $CO_2$ release mechanism may comprise a lever mechanism for opening the $CO_2$ container against the closing force of a container closing valve, and an actuator with a movable actuator part adapted to move between an activated position and a non-activated position.

Advantageously a maximum restoring force of the spring is smaller than the closing force of the container closing valve.

According to a preferred embodiment, the movable actuator part may comprise a main part and an additional part that is adapted to be fixedly coupled to the main part in different mounting positions, e.g. via a threaded joint, wherein the spring is coupled to the additional part. Preferably, the at least one clamping element, e.g. a plurality of clamping jaws, is coupled to the main part of the movable actuator part.

Furthermore, the liquid supply system may comprise a liquid level sensor unit provided in a water tank, said water tank being made from a conductive material and being connected to ground, the liquid level sensor unit comprising a power supply providing a predetermined voltage, a conductive sensor tip provided at a predetermined height over a bottom of the water tank, the sensor tip being electrically connected to the power supply via a resistor, and a device for detecting a voltage at a predetermined point between the resistor and the sensor tip.

When a conductive liquid, e.g. as normal line water including a given concentration of ionic impurities, is filled into the water tank, the supply system is adapted to detect that the liquid has reached the conducting sensor tip by a voltage drop occurring at the predetermined point between the resistor and the sensor tip.

According to a second aspect, the invention relates to a faucet comprising at least two internal conduits, preferably coaxial internal conduits, the internal conduits being separated, and preferably also thermally insulated, from each other. Although said faucet preferably may be a part of the water-based liquid supply system according to the first aspect of the invention, applicant also seeks independent protection therefor.

According to a third aspect, the invention relates to a soda machine comprising:
- a $CO_2$ container containing $CO_2$ at a $CO_2$ container pressure, e.g. 60 bar at 22° C.,
- a soda tank connected to the water supply and to the $CO_2$ container, the connection between the $CO_2$ container and the soda tank being free of a pressure reducer,
- a $CO_2$ release mechanism for releasing and injecting $CO_2$ gas from the $CO_2$ container directly into the soda tank through a nozzle located in the soda tank, the $CO_2$ release mechanism preferably comprising a lever mechanism for opening the $CO_2$ container and an actuator, in particular an electrical actuator, such as a solenoid actuator or an electrical motor, for operating the lever mechanism, and
- a check valve installed in the line connecting the $CO_2$ container and the soda tank and preventing $CO_2$ gas or water from flowing back from the soda tank towards the $CO_2$ container.

Although said soda machine preferably may be a part of the water-based liquid supply system according to the first aspect of the invention, applicant also seeks independent protection therefor.

According to a fourth aspect, the invention relates to a liquid level sensor comprising at least one electrode powered by an electrical voltage supply, the liquid sensor being adapted to detect an electrically conductive liquid in a grounded tank when the liquid enters into contact with the sensor. Although said liquid level sensor preferably may be a part of the water-based liquid supply system according to the first aspect of the invention, applicant also seeks independent protection therefor.

According to a fifth aspect, the invention relates to a UV sterilizing device adapted to sterilize a liquid in a tank or flowing through a pipe by irradiating it with UV light. Although said UV sterilizing device preferably may be a part of the water-based liquid supply system according to the first aspect of the invention, applicant also seeks independent protection therefor.

According to a sixth aspect, the invention relates to a control and communication system for controlling at least one smart device, in particular at least one smart kitchen appliance, the control and communication system being adapted to connect the at least one smart devices with communication capability, e.g. a liquid supply system, a hood, a cooker or the like, in such a manner that the smart device can communicate with a user and/or in case of at least two smart devices with each other, preferably by wireless communication, using short distance communication technology for activating, programming, and controlling the system, e.g. zigbi, Bluetooth or an equivalent technology. Although said control and communication system preferably may be a part of the water-based liquid supply system according to the first aspect of the invention, applicant also seeks independent protection therefor.

BRIEF DESCRIPTION OF THE DRAWINGS

FIGS. 8A and 8B show details of one possible embodiment of the $CO_2$ release mechanism for releasing $CO_2$ at high pressure from the canister before (FIG. 8A) and during (FIG. 8B) releasing the gas;

FIG. 10 shows an optional auxiliary $CO_2$ cycle connected to the soda tank;

DETAILED DESCRIPTION OF THE INVENTION

The present invention relates to a water-based liquid supply system, preferably a drinkable tap water-based liquid supply system, in particular in under-sink arrangement. The system may comprise a few or all of the following components, namely a faucet, a manifold, a control unit carrying out at least one software application, a water sterilizing system, and a wide variety of optional water-based supply reservoirs such as for boiling water, for hot water, for cold water, for soda water, flavor liquid tanks, "healthy liquids" reservoirs including healthy ingredients such as minerals, vitamins and others. The system may dispatch each of the selected liquids, but also a mix of the selected liquids, at a selected temperature and/or a selected concentration. For example, a mixture of soda and water for controlling the soda strength or a mixture of water and/or soda with optional liquid storages, such as flavor(s), vitamins, minerals or alike may be dispatched at a controlled concentration and temperature.

Furthermore, the afore-mentioned water-based liquid supply system, including in particular all of its afore-mentioned components, may be controlled by an advanced control system.

The water-based liquid supply system may be operated by an attached controller or a remote controller, and can be upgraded to higher levels of connectivity and operation by adding a local hub, a portable control unit, corresponding software applications, a connection to a cloud and add other additional features.

The water-based liquid supply system further allows direct user intervention, e.g. for controlling the dispatching process. For example, the user may desire to change the soda preparation process, e.g. by injecting $CO_2$, thus controlling the pressure in the soda tank, to control the soda flow rate and/or strength while dispatching the soda.

Furthermore, the water-based liquid supply system will allow to drain the faucet pipe from the liquid used recently whenever required, to avoid the mixing of two different liquids dispatched one after the other, for example when cold water or chilled water is required after using boiling water or when dispatching plain water after flavored water was used.

Figure 1:
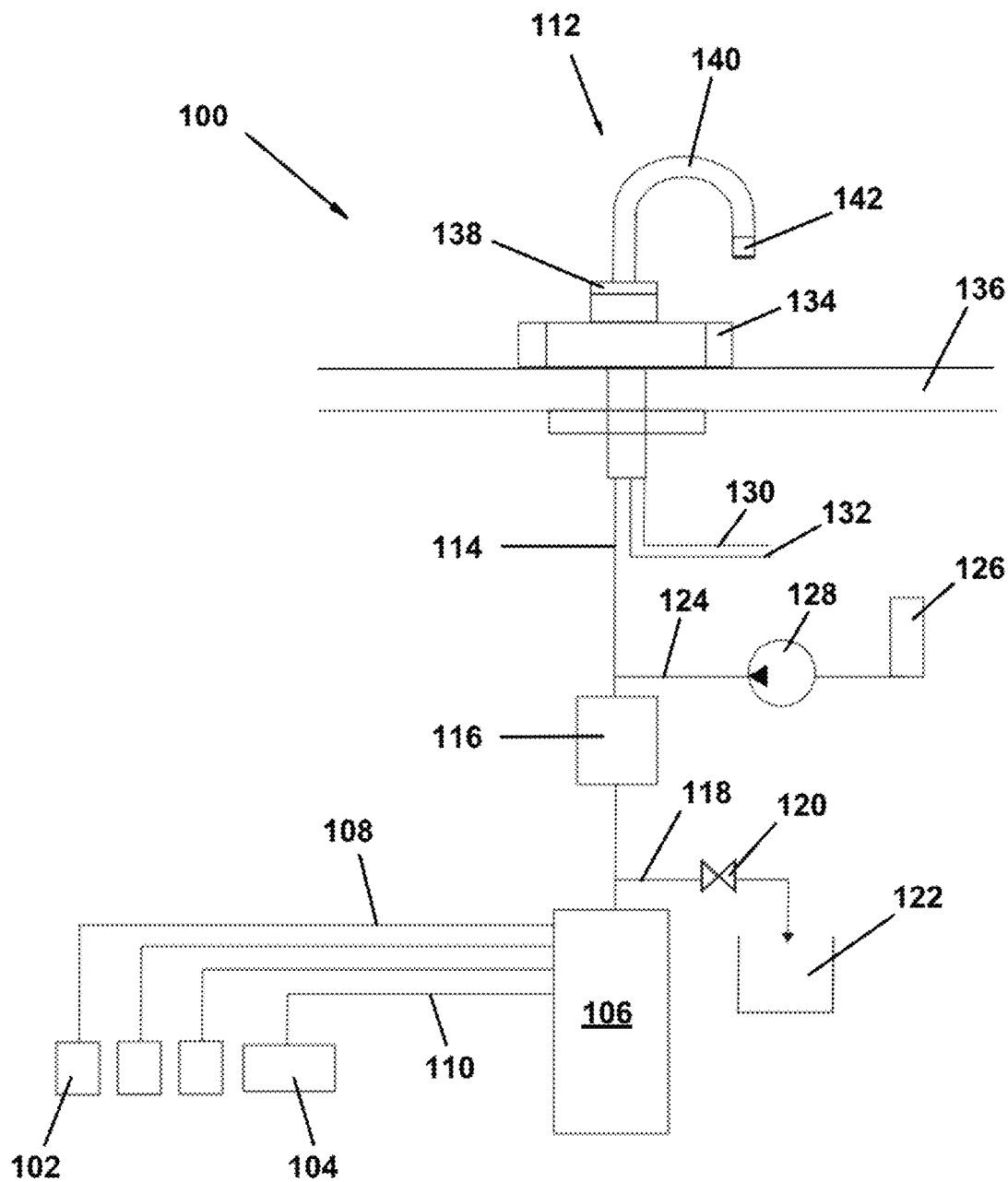
FIG. 1 schematically illustrates the components of a water-based liquid supply system as an example of a water-based liquid supply system according to the present invention.

FIG. 1 schematically illustrates the components of a water-based liquid supply system as an example of the present invention.

According to FIG. 1, the water-based liquid supply system generally designated 100 comprises under-sink tanks 102 and machines 104, which are connected to a manifold 106 by pipes 108, 110. The manifold 106 may contain consumable parts such as a water filter, a $CO_2$ canister and safety elements, like a safety group. The manifold 106 is connected to the faucet 112 by a pipe 114. A sterilizer 116 the operation of which is based on UV light that screens the water flow in the pipe 114 is optionally installed on the pipe line 114 after the manifold 106.

A pipe 118 branching off from the pipe 114 between the manifold 106 and the sterilizer 116 and including a solenoid valve 120 connects the pipe 114 to the drain 122 whenever required. For example, when the liquid selected to dispatch is different from the liquid previously selected, valve 120 opens and the liquid remaining in pipe 114 is drained by gravity (or optionally by a pump).

A pipe 124 connects between the pipe 114 and an additive liquid tank 126. A pump 128 is positioned on pipe 124 to inject the additive component into pipe 114 while the water-based liquid is consumed. Such an additive ingredient may be added for influencing the flavor of the liquid (flavor syrup) or for adding minerals, vitamins, coffee grains mix, soup or any other type. The system may contain one or more liquid additive tanks 126 for widening the mixing options.

Pipes 130 and 132 are connecting the water line (hot and cold) to the faucet 112. The faucet base 134 is attached to the countertop 136. It comprises a light emitting element 138 to indicate the type of water-based liquid dispatched. The faucet 112 further comprises a spout 140 connected to the fixed faucet base 134 and an aerator 142.

In the following, the water-based liquid supply system 100 according to the present invention and its components will be explained in more detail.

Figure 2:
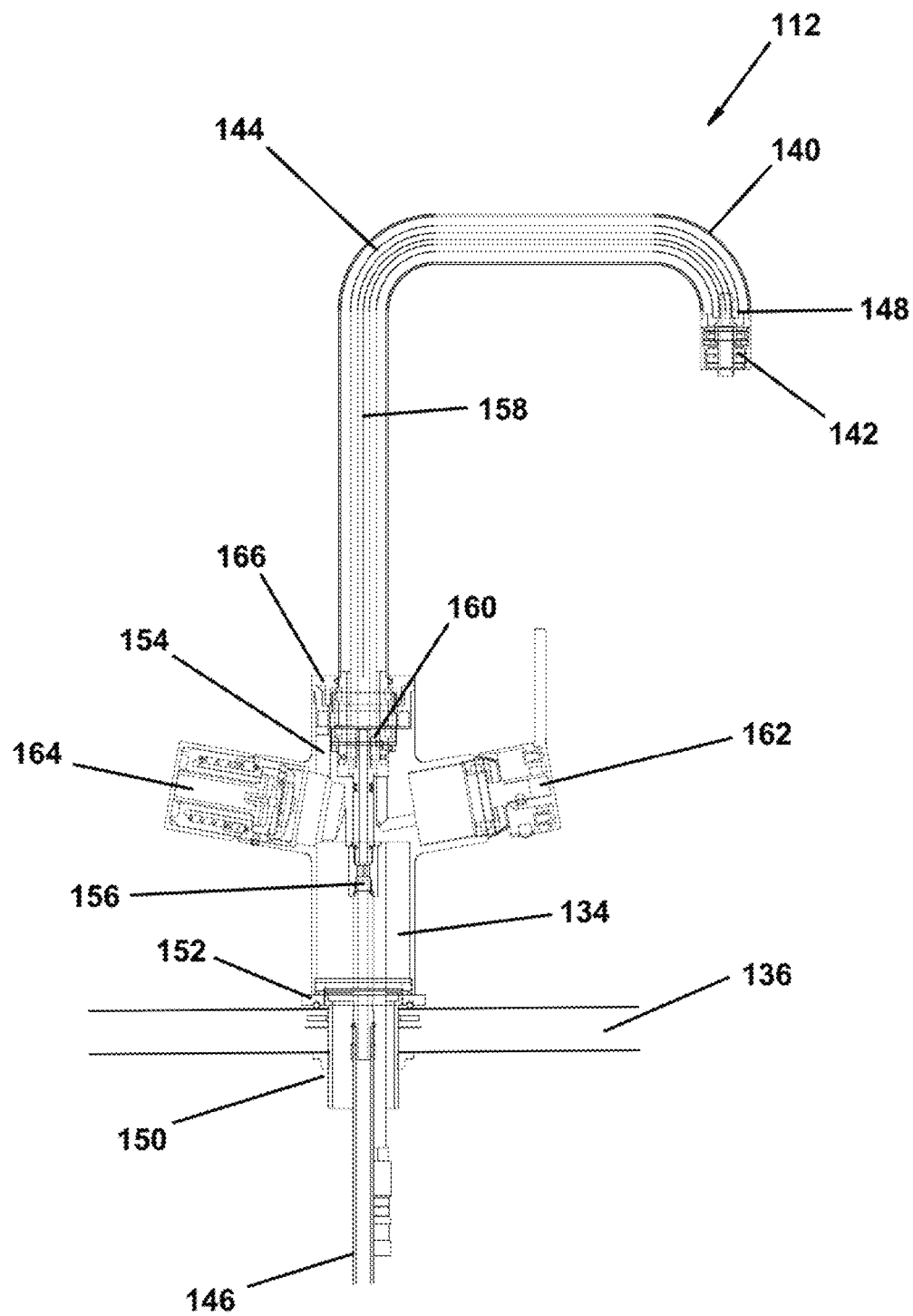
FIG. 2 shows a more detailed view of a faucet according to the present invention.

FIG. 2 shows a more detailed view of a faucet 112 according to the present invention.

The faucet 112 is suitable for isolating the different liquids dispatched therefrom, minimizing the heat and/or taste transfer between the various types of liquids dispatched. An isolating pipe 144 is inserted into the faucet 112 all the way from the inlet 146 of the faucet to the outlet 148. The pipe 144 inserted into the spout 140 may be internally divided in order to increase the number of conduits for better differentiation between the liquids dispatched.

The faucet 112 comprises a base unit 134 fixed to the countertop 136 by a nut 150 and a base shoulder 152. The swivel spout 140 is connected to the fixed base 154 and comprises an aerator 142. The internal conduit comprises an inlet pipe 156, which is connected to a further pipe 158 by an adapter 160, said adapter 160 and said further pipe 158 being designed to hold the drinking liquid and separate it from the line water.

The faucet 112 may include one or two knobs. In the embodiment of FIG. 2, two knobs are present, namely knob 162 for controlling the line water (e.g. non-purified water from the main) and knob 164 for selecting the type of liquid and dispatch it.

Knob 164 has a light indicator 166 indicating the type of liquid chosen and signaling it by changing between a plurality of at least two colors. The light changes when the knob 164 is turned. Alternatively or additionally, the knob 164 and/or the entire system 100 may provide an audio signal in response to a change in selection. The light indicator 166 may be a built-in light indicator or may be located on the fixed faucet base 154. According to the present invention, knob 164 may be referred to as an "electrical knob" or "e-knob".

Figure 3:
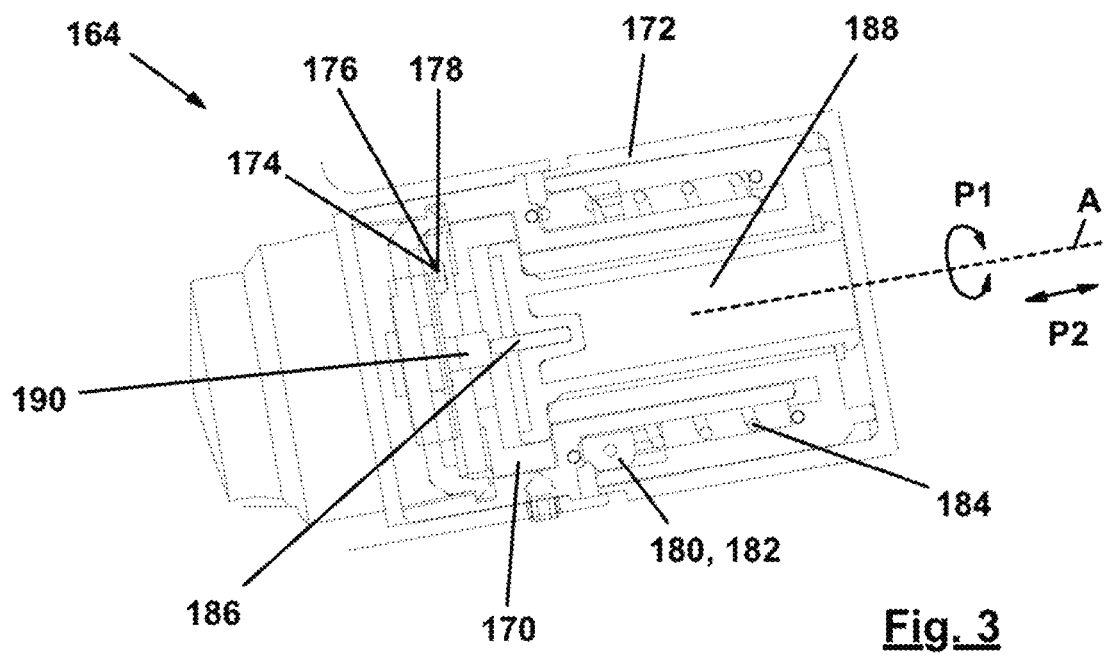
FIG. 3 shows an enlarged view of an e-knob of the faucet of FIG. 2.

FIG. 3 shows an enlarged view of an e-knob 164. The e-knob 164 according to the present invention may perform a bidirectional rotational movement around axis A as indicated by double-arrow P1 as well as a bidirectional axial movement as indicated by double-arrow P2, the rotational movement serving for selecting the type of liquid to be dispatched and the axial movement serving for dispatching the selected liquid.

When turning the outer shell 172 of e-knob 164, an internal reflecting element 170 is rotated together with the outer shell 172 and changes the intensity of the light reflected from its surface. The reflecting element 170 may be provided as a reflecting ring, but preferably is provided as a reflecting disc. Light emitted by an LEDs 174 positioned on a printed circuit board 176 illuminate the rotating reflecting element 170. Optical sensors 178 on the printed circuit board 176 detect the light reflected from the reflecting element 170, and sense the change of the intensity of the reflected light when the reflecting element 170 is turned.

A step mechanism 180 including a step element 182 biased by a spring 184 mechanically divides the circumferential rotation of e-knob 164 into a predetermined number of steps, e.g. twelve steps, which may be clearly differentiated from each other by an user. Each step of rotation results in a change of the color displayed on the faucet light ring 166 in a predefined sequence representing the available types of liquids. When the desired liquid's color is displayed, an axial movement of the e-knob 164 will result in dispatching the selected liquid.

The rotation of the reflecting element 170 is synchronized with the circumferential steps of the e-knob 164. Each step of the e-knob 164 results in a change of the reflection sensed by at least one of the sensors 178 on the printed circuit board 176. The arrangement of the sectors on the reflecting element 170 and the position of the LEDs 174 result in a change of the reflected beam sensed by the sensors 178, which in turn results in a change of the signal sent to the e-knob's control unit 186. The control unit 186 analyzes the direction of rotation of the e-knob 164 and the number of steps. Each of the steps results in a change of the selected liquid, and is presented to the user by the light color displayed, for example on the light ring 166 of the faucet 112.

An axial movement of the e-knob 164 will move a pin 188 towards a detector 190 placed on the printed circuit board 176 and will result in dispatching the type of liquid presented on the light ring 166.

In the following the operation of e-knob 164 and the interpretation of the signals output from optical sensors 178 by the control unit 186 will be discussed in more detail referring to FIGS. 4A to 4C.

In order to allow the detection of twelve steps per full rotation of the e-knob 164 around axis A, the reflecting element 170 is divided into six sectors having alternating high and low reflectivity. In FIGS. 4A to 4C, a sector of high reflectivity is indicated by white color, whereas a sector of low reflectivity is indicated by black color. Two optical sensors 178a and 178b are located in close vicinity to the reflecting element 170. As each sector covers a circumferential angle of 60°, i.e. 360° divided by half of the number of steps, the two optical sensors 178a and 178b have a circumferential distance of 30°, i.e. half of the circumferential range covered by one sector. Furthermore, in a starting position shown in FIG. 4A, the two sensors 178a and 178b are located over one and the same sector having a circumferential distance from the edges of this sector of 15°, i.e. a quarter of the circumferential range covered by the sector. Accordingly, both optical sensors 178a and 178b output a high-level signal to the control unit 186.

Figures 4A, 4B:
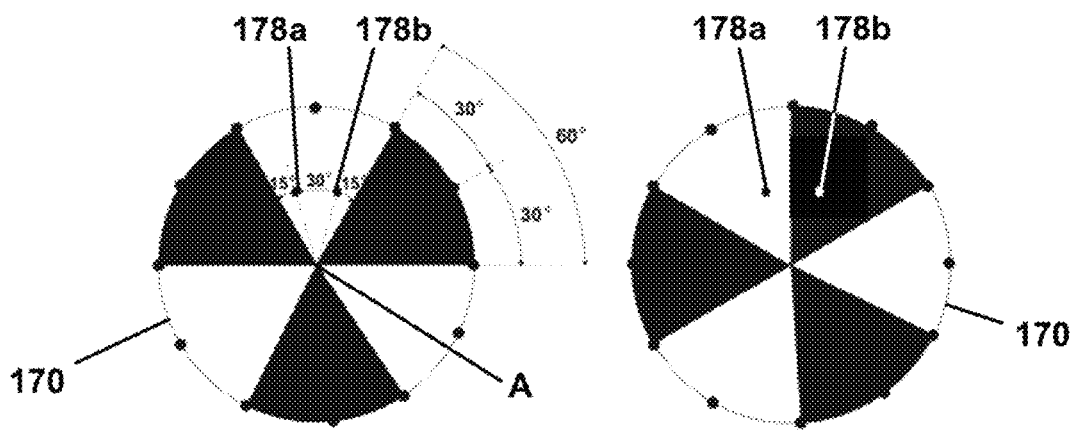
FIGS. 4A to 4C illustrate the interpretation of the signal output from the optical sensors of the e-knob of FIG. 3.

Refer now to FIG. 4B. Turning the outer shell 172 by one step, i.e. turning the reflecting element 170 by 30°, results in the sensor 178b being positioned over a black sector, while sensor 178a remains over the white sector. As a consequence, optical sensor 178a continues to output a high-level signal to the control unit 186, whereas optical sensor 178a now outputs a low-level signal to the control unit 186. Accordingly, a change from same level output to different level output signals a one step rotation.

Figure 4C:
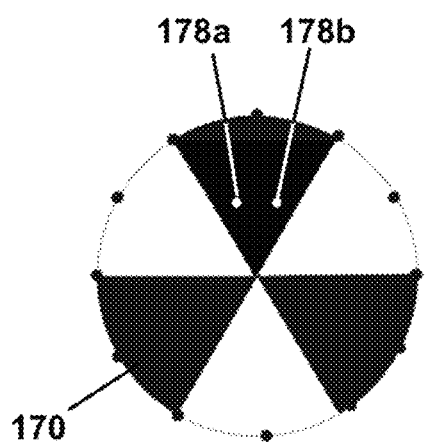

Referring to FIG. 4C, the outer shell 172 has been rotated again in the same direction by one step, i.e. by 30°. Now, both optical sensors are located over a black area, and both send low-level signals to the control unit 186.

The afore-described arrangement furthermore allows detecting the direction of rotation. When starting from an equal-level situation, i.e. a high level-high level situation (HH) or a low level-low level situation (LL), the first level indication referring to sensor 178a and the second level indication referring to sensor 178b, a change of the signal level of sensor 178b indicates a clockwise turn ( . . . -HH-HL-LL-LH-HH- . . . ), as in the afore-described example, whereas a change of the signal level of sensor 178a indicates a counter-clockwise turn ( . . . -HH-LH-LL-HL-HH- . . . ). And when starting from a differing-level situation, i.e. a high level-low level situation (HL) or a low level-high level situation (LH), sensor 178b maintaining its signal level indicates a clockwise turn, as in the afore-described example, whereas sensor 178a maintaining its signal level indicates a counter-clockwise turn.

The detection method according to the present invention is different from standard rotation detection methods. While the standard methods detect intensity changes while the reflecting element moves from one sector to another section, i.e. detects the signal transition, the method according to the present invention detects the sector where the LEDs and the sensors are positioned after it has been made sure by the step mechanism 180 that the new sector has been reached, i.e. detects the signal in its steady state. As a consequence, slower sensors may be used.

In addition, it should be noted that the division into twelve equal steps by providing three areas of high reflectivity and three areas of low reflectivity as well as two sensor units, is used by way of example only. Other divisions might be used as well.

The separation of the different liquids dispatched in the spout is achieved by inserting a plurality of pipes into the faucet spout 140. However, this option is practically limited and difficult to implement. The faucet spout 140 must be kept free for swiveling and the tubes inside may be twisted and damaged. Furthermore, the sealing of the pipes may be challenging. The invented faucet proposes the solution of one pipe divided internally to allow separate flow of different liquids.

The faucet 112 includes an aerator 142 attached at the tip of the faucet 112, which is specially adopted to the water-based liquid supply system which may provide a wide range of water-based liquids having differing properties. The faucet aerator 142 allows maintaining a suitable liquid stream when the liquid is line water (hot and cold), on one hand, or drinking water such as hot or boiling water or soda, on the other hand. Prior art aerators, for example, create a non-splashing stream, shaping the water stream to be centered, and delivering a mixture of water and air. The aerator 142 according to the present invention is designed to create a specifically required stream shape for various water-based liquids such as soda or boiling water, while keeping the line water flowing in another stream shape. Soda (carbonated water, or seltzer) contains $CO_2$ gas. Direct splash onto the bottom of the receiving vessel may cause a turbulent flow resulting in $CO_2$ diffusion from the soda or even jumping out of the vessel. Boiling water is provided from a boiler tank that might be under high pressure caused by the water steam in the tank and may result in jumping out of the vessel if directed to the bottom of the receiving vessel.

The aerator 142 according to the invention directs the drinking liquid like the soda stream and the boiling water to the vessel spread towards the vessel walls without crossing any obstacle such as a mesh or small plastic halls while flowing into the receiving vessel accumulating the liquid dispatched. Spreading the stream will also slow the liquid velocity and reduce the impact of hitting the bottom of the vessel.

Figure 5:
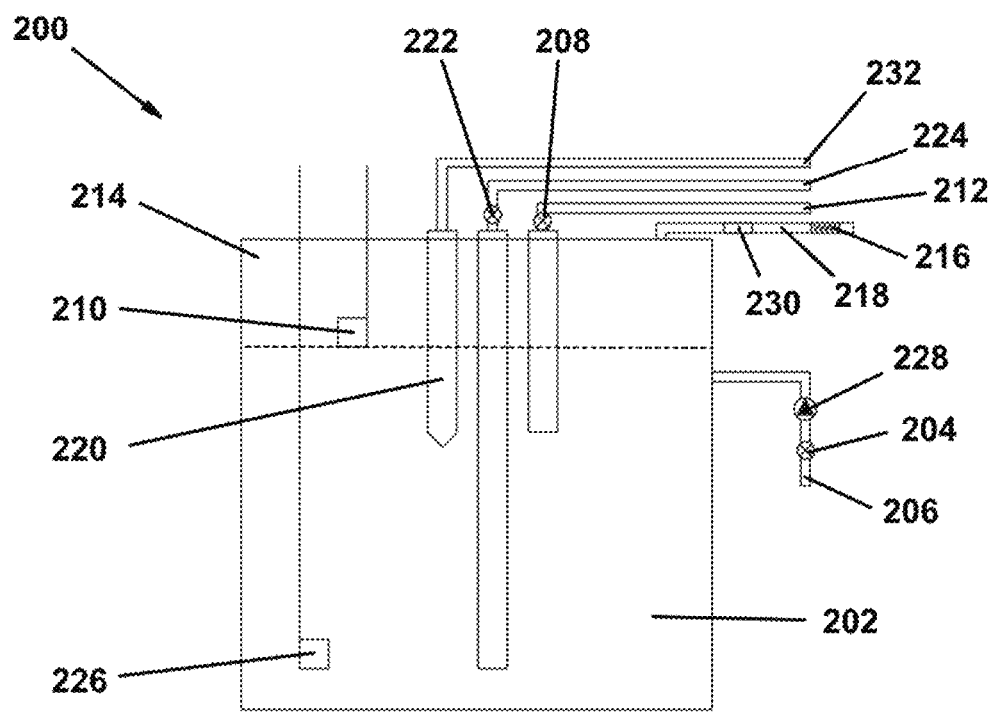
FIG. 5 shows a schematic view of a carbonation machine according to the present invention.

FIG. 5 shows a schematic view of a carbonation machine 200, also called soda machine 200, according to the present invention.

The carbonation machine according to the present invention is proposed for preparing, storing and dispatching soda from an internal permanent vessel to be consumed whenever required. The soda is delivered at a required condition and concentration by controlling the soda preparation process parameters, and optionally mixing it with chilled water or other additive(s) while consuming.

The soda machine according to the present invention may be integrated in the water-based liquid supply system, and optionally include smart control, including short-distance communication capability, such as Bluetooth®, and long-distance communication capability, such as Wi-Fi® connectivity to the internet. The soda machine may be operated either directly using an attached control unit or via a smart device application.

The wide soda preparation options, including parameters setting, operation cycles, pressure and mixture control, allows various soda strength levels and mixing possibilities with chilled water or other ingredients, provides a new way for full flexibility controlled by the user. For example, the user may decide on the soda strength on each portion dispatched by mixing water (or chilled water) to existing stored soda in order to reduce the soda strength or define the amount of soda to be consumed. The proposed process of mixing the soda with water while consuming increases the soda volume available at one preparation cycle.

The soda machine according to the present invention may include a pressure sensor, used e.g. in the context of alerting for $CO_2$ canister or $CO_2$ cylinder replacement, and provides input on the soda on preparation process or the stored pressure.

It is anticipated that the $CO_2$ gas may leak at a certain time from the tank. To maintain the soda stored in the tank at a desired pressure, $CO_2$ gas may be periodically injected. A pressure sensor connected to the soda container may detect the pressure in the soda tank in order to allow for a pressure alert being output.

An optional auxiliary tank may be connected to the soda tank for absorbing excess $CO_2$ gas injected to the soda tank, and returning it to the carbonation tank. A pressure relief safety valve may be used for controlling the pressure in the auxiliary tank, in addition or as an alternative to other safety measures used for controlling the pressure in the $CO_2$ tank.

The use of the auxiliary tank in the secondary cycle provides few advantages such as:

Higher safety in operation together with the pressure sensor, as three levels of independent pressure control may be provided. The internal relief valve, i.e. the relief valve inside the auxiliary tank, may be set at a pressure p1, whereas the external relief valve, i.e. the relief valve outside the auxiliary tank, may be set at a pressure p2, which is higher than p1, and the pressure sensor may be set at a pressure p0, which is higher than p1, but smaller than p2.

It eliminates the need for connecting the system to drain for draining the water exhausted, i.e. the water drops released together with the $CO_2$. It collects water drops and returns them to the soda container.

It saves $CO_2$ and water by recycling them when exhausted.

It lowers the noise of the exhaust $CO_2$. It prevents the external pressure relief valve to open and release air out of the system.

It eliminates the need for separation of the $CO_2$ gas and water drops that are exhausted out together with the excess gas as it is returned to the water tank together with the gas.

The soda machine comprises a newly invented liquid level sensor for detecting the water level in the tank.

The soda machine is optionally combined to a water tank. Both tanks may be cooled. A newly invented method called "twin cooling cycle" maintains the desired temperature in each of the tanks.

The system is controlled by one or more of the options described and including among others: A dedicated controller, software applications for smart devices and Wi-F® for indoor and outdoor communication. The software applications are designed to follow the system's performance, control it and detect possible failure remotely. The use of consumable parts is followed up and a replacement/end of lifetime alert is provided on lime. The unit may also be operated by voice commands, either directly or via a voice assistance device. The proposed process of soda preparation may be controlled by the control unit. However, a manual interruption option is available in order to manually override the electrical control of the unit.

The carbonation tank 202 shown in FIG. 5 is designed to mix water, preferably at low temperature, with $CO_2$ gas. When a user operates the soda machine 200, valve 204 on pipe 206 opens and water flows into the tank 202. The pipe 206 may be connected to the main water line or to a tank of chilled water. To keep the flow fluent and prevent a pressure increase in the tank 202 while supplying the water, relief valve 208 may be opened to release the air replaced by water flowing in. When the water reaches an upper level the upper level sensor 210 detects the water and sends a signal to the control unit to stop the flow of water into the tank 202 by closing valve 204. Then, the relief valve 208 is closed, and $CO_2$ gas is injected into the pressure vessel 202. The $CO_2$ is injected at high pressure for efficient mixing of the gas in the water.

Alternatively, the system may be designed to work without water level sensors, e.g. when the sensors are damaged or not assembled. When the upper level sensor 210 is not active, the water flow into the tank 202 may be controlled by a timer.

When too much water flows into the tank 202, it flows out through the relief pipe 212 while valve 208 remains open. The inlet of relief pipe 212 is positioned at a certain level below the upper ceiling of tank 202 in order to create a gas trap space 214 at the top of the tank 202, i.e. between the inlet of pipe 212 and the top of the tank 202.

The gas trap space 214 is required for the soda preparation process. The $CO_2$ gas is injected into the water, a part of it being dissolved in the water, while another part of the $CO_2$ is accumulated above the water level in the gas trap space 214. A pressure relief valve 216 connected to the tank 202 by pipe 218 limits the pressure in the tank.

A gas nozzle 220 connected to the $CO_2$ canister via a pipe 232 is positioned at the top of the carbonating tank 202. For injecting the $CO_2$ into the water, when water fills the soda container 202, the $CO_2$ is injected directly from the $CO_2$ cylinder at a very high pressure held in the $CO_2$ tank (about 60 bar). When soda is ready for use valve 222 is opened and the soda is forced to flow out of the tank 202 by the pressure in the tank 202 via pipe 224. The entrance of pipe 224 is located at the bottom of the tank 202. When the soda level reaches the lower level sensor 226, the sensor 226 sends a signal to the controller 500 to have the lank 202 refilled with water. When the sensors 210 and 226 are out of work or not installed, the machine controller 500 calculates the accumulated soda consumption and, when it reaches the amount equal to the tank volume, the control unit opens valve 204 to refill the tank 202. A one direction valve 228, e.g.

constructed as a check valve, is positioned on the pipe 204 to prevent backflow, when the pressure in the tank 202 is above the line pressure.

A pressure sensor 230 assembled in a pipe communicating with tank 202, for example pipe 218, detects the pressure in the tank 202. One reason is to maintain the pressure and the flow of the soda out of the tank 202 constant. The sensor 230 may regulate the $CO_2$ injection to the level required and maintain the internal pressure, in case gas should leak out. When injection of the $CO_2$ does not result in an increase of the pressure in the tank 202, the control unit 500 outputs an alert for need to replace the empty $CO_2$ canister. The pressure sensor 230 is used as additional safety device to limit the pressure in the tank 202 in parallel to the mechanical safety pressure relief valve 216.

Figure 6:
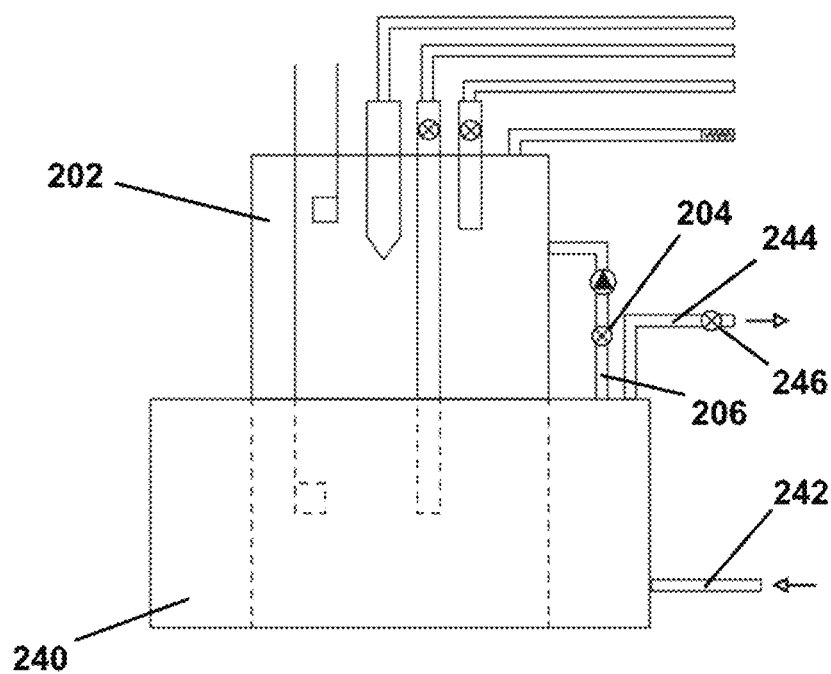
FIG. 6 shows an embodiment including a combination of a soda tank with a water tank.

FIG. 6 shows an embodiment including a combination of the soda tank 202 with a water tank 240.

According to the present invention, the soda tank 202 may optionally be merged into a supply tank 240 for chilled water built to provide chilled water for consumption or for filling the $CO_2$ container.

The water container 240 partially surrounds the soda container 202 exposing the upper part thereof for optional direct cooling.

The water tank 240 includes a water inlet pipe 242 connected to the main water line (preferred filtered). An outlet pipe 244 with a valve 246 serves as an outlet for water to be consumed. Again the pipe 206 with a valve 204 connects the water tank 240 to the soda tank 202 for supplying water to the carbonating tank 202 whenever valve 204 opens. The main water line fills the water tank 240 whenever water is consumed due to one of the valves 204 or 246 being opened.

The two tanks 240 and 202 are simultaneously cooled by a refrigeration unit (not shown in FIG. 6). Soda is mixed most efficiently at a low temperature, for example 5° C., while cold water is preferably consumed at a higher temperature, for example 10° C. In order to satisfy the different temperature requirements of the two tanks 240 and 202, the refrigeration unit allows cooling the two tanks at different cooling rates. The cooling power for each of the tanks 240 and 202 may be controlled in various alternative ways, for example by utilizing different numbers and/or different lengths of coils of the cooling system wrapping each of the tanks 240 and 202.

In this arrangement water tank 240 is connected to the main water line (preferred filtered) directly via inlet pipe 242 keeping the pressure in the water tank 240 at the main water line pressure. The water tank 240 is filled whenever water from the tank is required to be consumed or to fill the soda tank 202.

The water tank 240 has two optional outlets. Outlet pipe 244 is connected to the faucet 112 controlled by valve 246. When valve 246 opens, water flows from the water tank 240 out to the faucet 112. Moreover, pipe 206 connects the water container 240 with the soda container 202. Whenever valve 204 positioned on pipe 206 opens, water flows into the carbonation tank 202 and fills it up, while the afore-mentioned air relief valve 208 is kept open to prevent a pressure rise in the tank 202, thus eliminating the need for an on/off valve or a pressure regulator.

The $CO_2$ gas is injected via a pipe 224 and nozzle 222 (see FIG. 5). The direct injection of $CO_2$ into the water in the carbonating tank 202 results in a high turbulence stream with high efficiency of gas mixing, one direction flow control unit 248 (see FIG. 11A) positioned on pipe 232 prevents the $CO_2$ gas or soda water from flowing back from the carbonation container 202 towards the $CO_2$ container 260 (see FIG. 7), e.g. when the $CO_2$ container 260 is released for replacement. The pressure relief valve 216 located on pipe 218 accordingly secures that the maximum pressure in the tank doesn't exceed the pressure relief setup. A pressure sensor on the pipe senses the pressure when injecting $CO_2$ to the tank and, if pressure during injection is low, it sends a signal to the control unit 500 to indicate that the $CO_2$ container 260 needs to be replaced. However, if the pressure in the tank 202 exceeds the maximum set pressure, the sensor sends a signal to the control unit 500 to stop the injection of the gas. This arrangement of pressure detection by sensor and relief valve, both optionally located in the manifold still to be described) is required due to the high pressure in the $CO_2$ tank 202.

Figure 7:
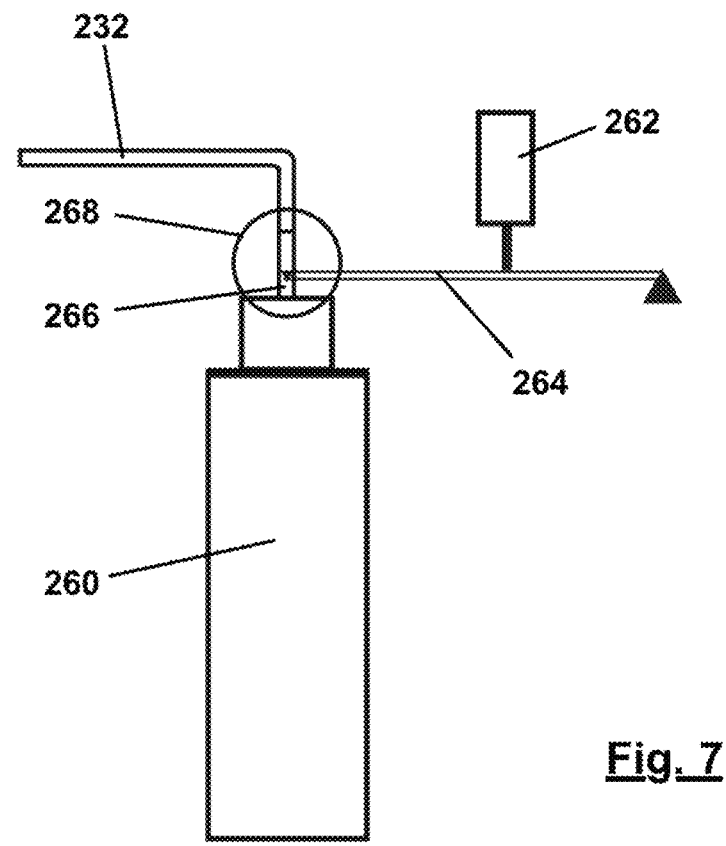
FIG. 7 schematically shows a $CO_2$ gas canister.

FIG. 7 schematically shows the $CO_2$ gas canister 260, also referred to as $CO_2$ container, which is connected to the carbonation tank 202 via pipe 232. A solenoid actuator 262 pushes the lever 264 and presses the canister paintball 266 to release the $CO_2$ gas from canister 260 at high pressure and to inject it to the soda tank 202. One direction valve 248 (see FIG. 11A) prevents the gas from flowing back when replacing an empty canister 260.

FIGS. 8A and 8B show details of one possible embodiment of the $CO_2$ release mechanism 268 for releasing $CO_2$ at high pressure from the canister 260 before (FIG. 8A) and during (FIG. 8B) releasing the gas.

FIG. 8A shows the $CO_2$ release mechanism 268 before the lever 264 is pressed. When the lever 264 is pushed down (FIG. 8B), the lever 264 presses the guide pin 270 down pressing the paintball 266 of $CO_2$ canister 260 and releasing $CO_2$ gas stream (illustrated by arrow P3). The one direction valve 248 (see FIG. 11A) located along the pipe 232 prevents the $CO_2$ from return back to the $CO_2$ release mechanism 268.

Figure 9:
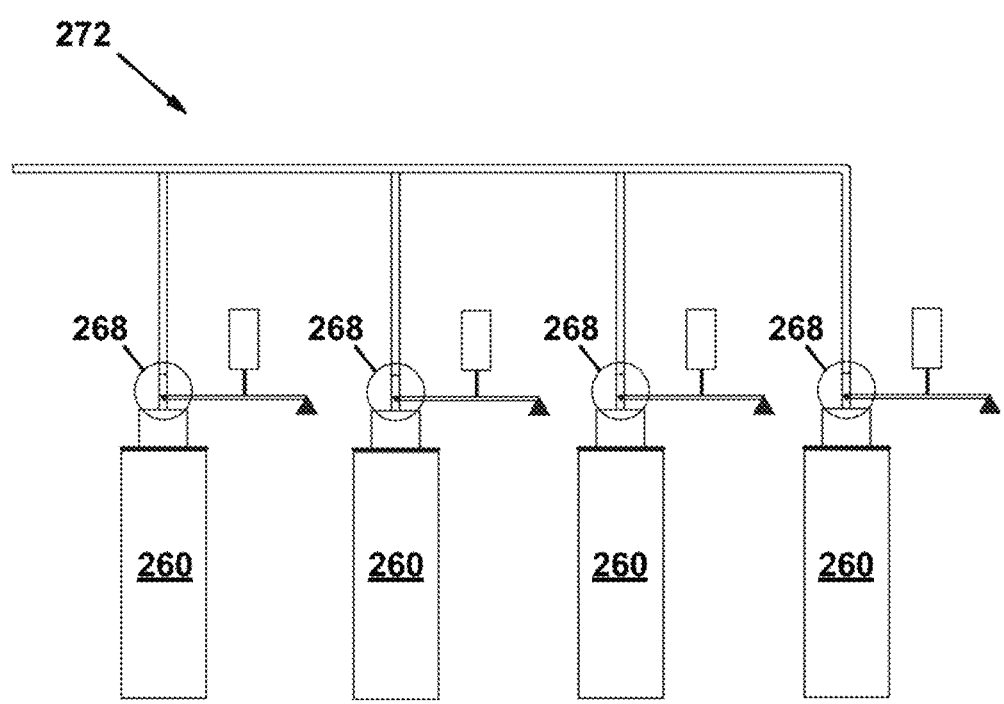
FIG. 9 shows a magazine including a plurality of $CO_2$ canisters.

FIG. 9 shows a magazine 272 including a plurality of $CO_2$ canisters 260 each being equipped with a $CO_2$ release mechanism 268 as shown in FIGS. 7, 8A and 8B. The multi-canister magazine of FIG. 9 allows reducing the maintenance intervals needed for cylinder replacement. The system controller 500 may provide a message to inform the user about the remaining un-used $CO_2$ containers 260 in the magazine 272. When only one unused $CO_2$ canister 260 is left, the system controller 500 sends an alert to the user and optionally to a service provider to prepare a new set of canisters 260 to refill the magazine 272.

FIG. 10 shows an optional auxiliary $CO_2$ cycle 280 connected to the soda tank 202. The auxiliary cycle 280 comprises a pipe 282 connecting between the carbonation tank 202 and expansion tank 284. When the pressure in the carbonation tank 202 and the pipe 282 exceeds the pressure p1 set in the relief valve 286 (connected to the pipe 282), the pressure relief valve 286 opens and releases $CO_2$ gas possibly mixed with water drops from the carbonation tank 202 into the expansion tank 284 until the pressure in tank 284 and the pressure p1 set on the relief valve 286 exceed the pressure in the carbonation tank 202.

When the pressure in the tank 284 is above the pressure in the carbonation tank 202 (for example due to the soda consumption or leakage in the system), the $CO_2$ and water drops accumulated in the tank 284 flow back to the carbonation tank 202 through pipe 288 and one-directional valve 290 balancing the pressure between tank 284 and the carbonation tank 202. The pressure relief valve 286 prevents the flow to the carbonation tank 202 through pipe 282.

A noise reduction element may optionally be added for reducing the noise level when the $CO_2$ gas and water drops flow into the expansion tank 284. The one-directional flow valve 290, optionally constructed as a check valve, on pipe 288 prevents the flow of $CO_2$ gas, soda and water backward from the carbonation tank 202 into the expansion tank 284 through pipe 288. A second pressure valve 292 may be connected to the entry of the auxiliary device 280. It may be set to a pressure p2 higher than the pressure p1 to prevent the pressure in the $CO_2$ tank and auxiliary device 280 from exceeding the pressure p2.

Figure 11A:
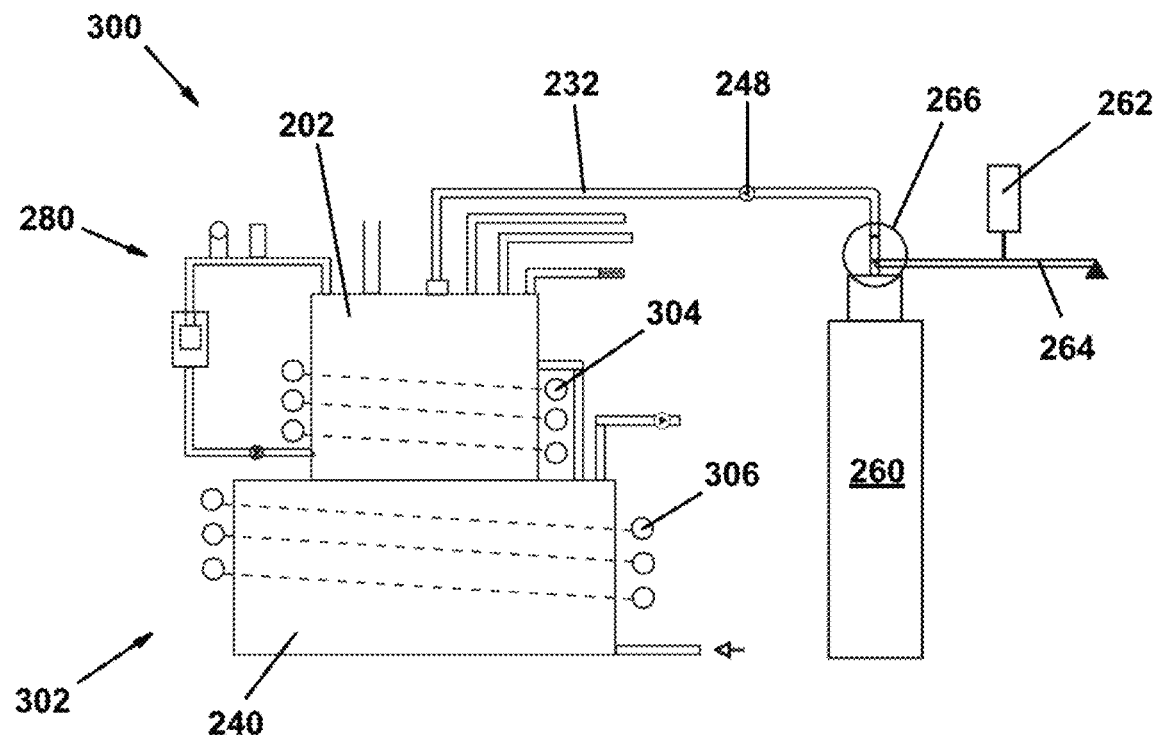
FIGS. 11A and 11B show the combined soda and chiller system including an optional arrangement of the two-level cooling system with the carbonation tank semi-merged in water chilling tank.
Figure 11B:
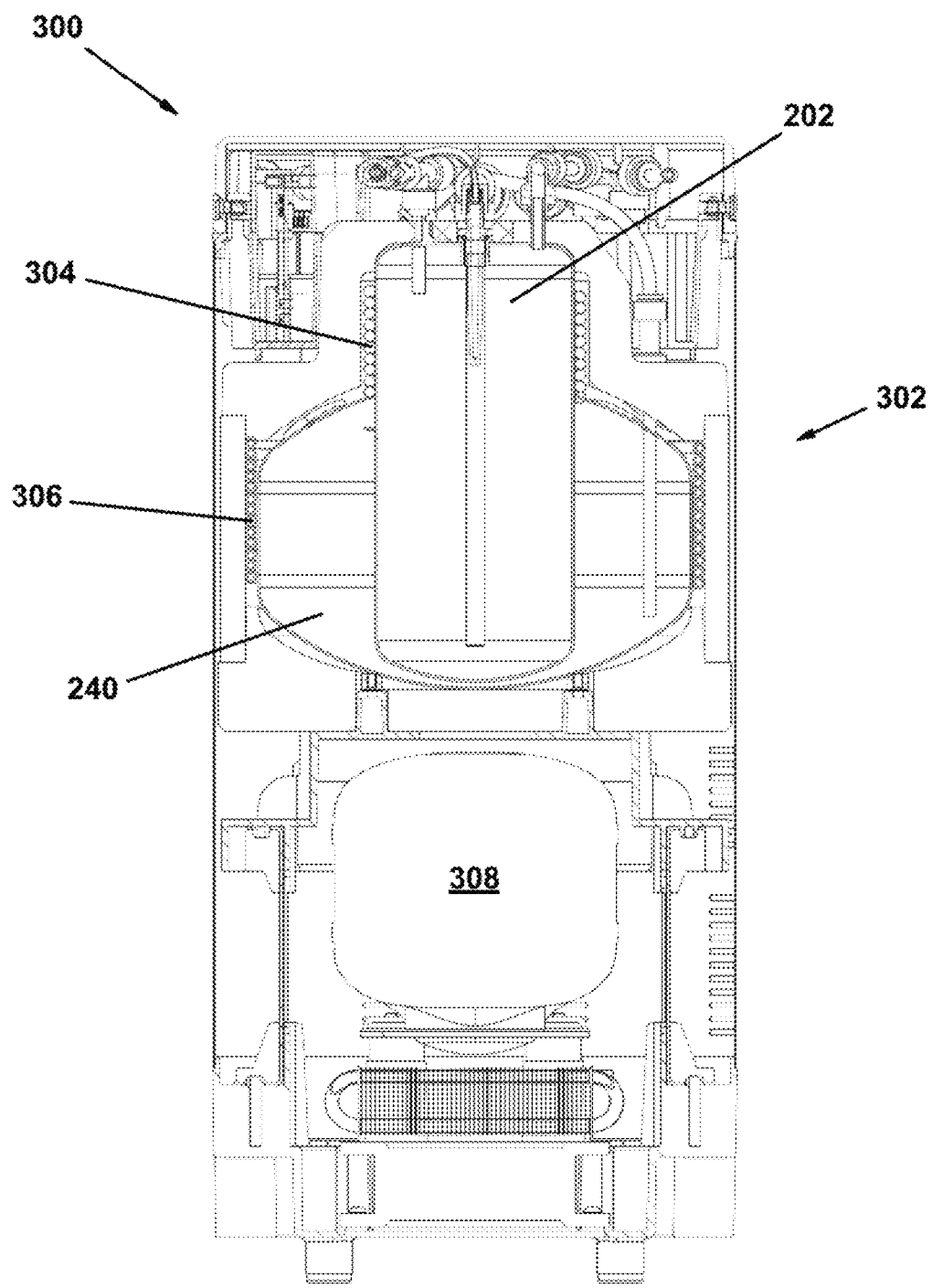

FIGS. 11A and 11B show the combined soda and chiller system 300 including an optional arrangement of the two-level cooling system 302 with the carbonation tank 202 semi-merged in water chilling tank 240. Coil pipes 304 of the cooling system cool the soda tank 202 directly, and pipes 306 of the cooling system cool the water tank 240. The direct cooling of the soda tank 202 also accelerates the cooling of the water tank 240 that is now cooled from both sides, namely its external wall and its internal wall, thus minimizing the temperature gradient along the tank radius.

The cooling proposed in this invention simultaneously cools the two separate containers, i.e. the water chiller container 240 and the carbonation container 202. An adequate amount of cooling is provided to each of the tanks 202, 240. Temperature sensors and microcontroller may be arranged to detect the temperature on each tank 202, 240, thus enabling the system to reach optimal temperatures.

Although the example shown presents cooling of two separate tanks, the concept could be used for further purposes as well, for example the cooling water tank 240 and an ice tank etc.

Figure 12:
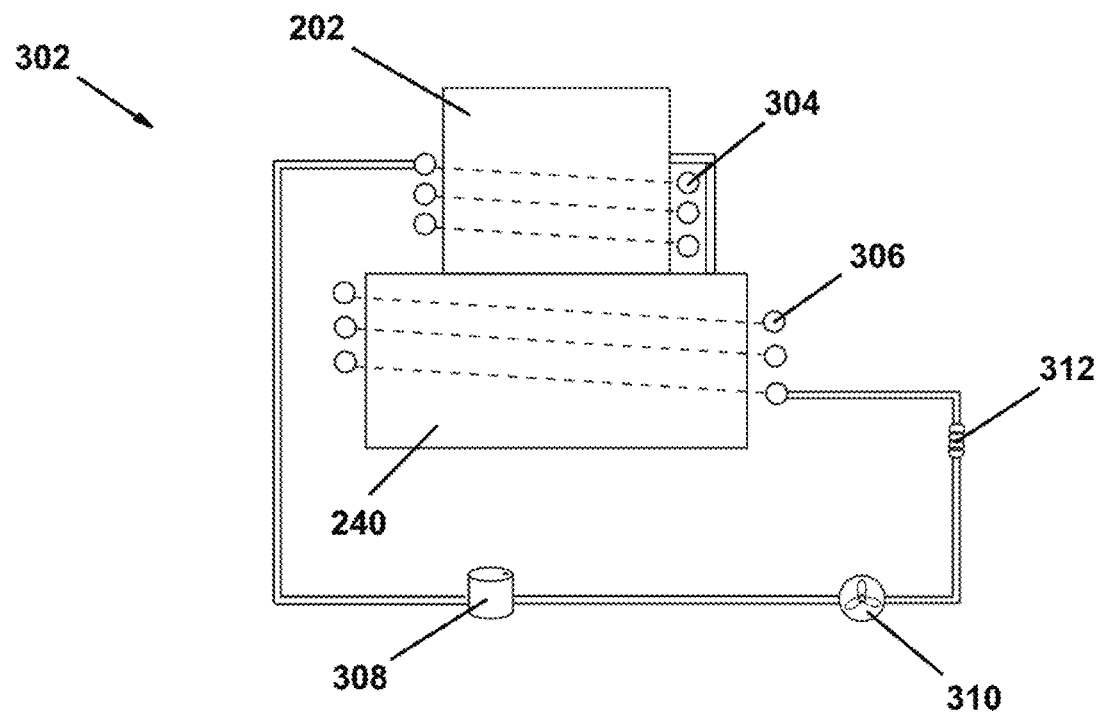
FIG. 12 shows details of the multi-cooling cycle.

FIG. 12 shows details of the multi-cooling cycle 302. The refrigerant flows from the compressor 308 which rises the refrigerant pressure to the condenser 310 where it condenses from vapor to liquid, while releasing heat to the surrounding. Then the refrigerant goes through the expansion valve 312, which causes the refrigerant to experience a pressure drop. Then the refrigerant goes to the "evaporator", i.e. the cooling coil pipes 304, 306, and draws the heat from the tanks 202 and 240 while vaporizing the refrigerant. The vaporized refrigerant returns to the compressor to restart the cycle.

Thus, an adequate amount of cooling is provided to each of the containers 202, 240. It may be generated by either designing proper cooling pipe lengths for each of the containers to draw the adequate heat amount from each of the containers 202, 240, or by any alternative design arrangement.

Figure 13A:
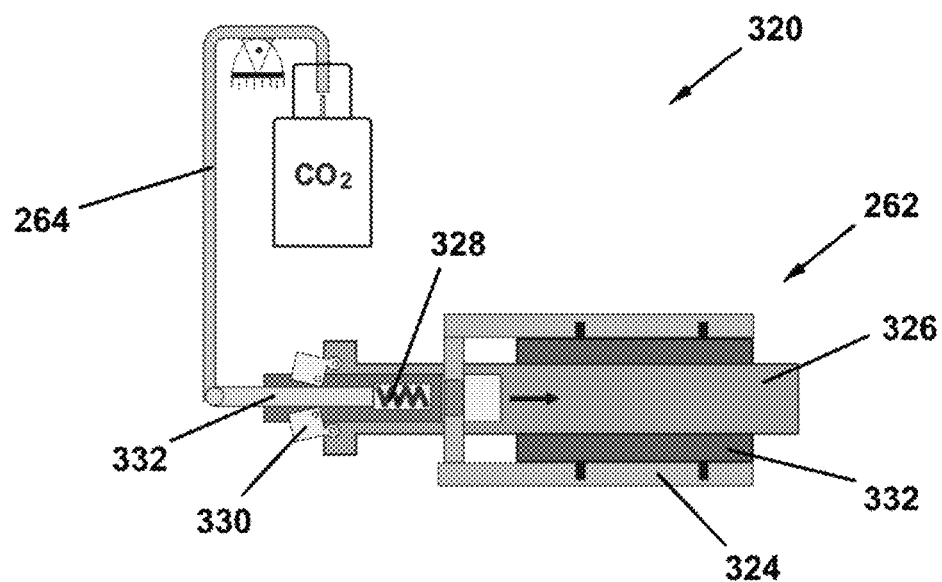
FIGS. 13A and 13B show the gap control mechanism in two positions, "non-activated" (FIG. 13A) and "activated" (FIG. 13B)
Figure 13B:
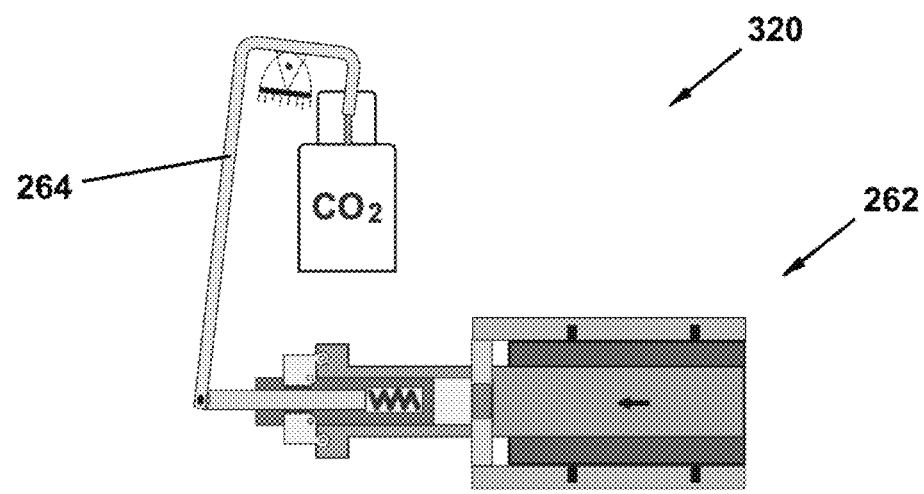

FIGS. 13A and 13B illustrate an gap control mechanism 320 for excluding any gap possibly existing in the $CO_2$ injection device.

The soda machine 200 according to the present invention requires the injection of $CO_2$ from the $CO_2$ canister 260 to the carbonation tank 202. The pressure in the $CO_2$ canister 260 is high and therefore the power required for pushing the paintball 266 and release the $CO_2$ is very strong. To reduce the power required from the solenoid 262, in order to reduce the solenoid size and the current required, a lever 264 may be used. However, the use of the lever 264 increases the required solenoid stroke. In addition to this effective stroke required for pushing the paintball 266 from its closed position to its opened position, there also is an ineffective stroke for closing the free gap between the solenoid 262, the lever 264 and the paintball 266, this gap being due to tolerances accumulated such as changing locations of the $CO_2$ canister 260 when replacing a used canister with a new one, paintball 266 height in the different $CO_2$ canisters 260, and the mechanism connecting the two parts.

The gap control mechanism 320 according to the present invention closes the gaps between the mechanical structure parts between the solenoid 262 and the paintball 266 whenever the solenoid 262 is not activated, for example, when replacing a used $CO_2$ canister 260 by a new one.

FIGS. 13A and 13B show the gap control mechanism 320 in two positions "non-activated" (FIG. 13A) and "activated" (FIG. 13B).

When the solenoid coil 322, which is held by a frame 324, is not activated, solenoid pin core 326 is pushed back (i.e. to the right in FIG. 13A) by the closing force of the $CO_2$ paintball 266 pin which is transferred to the solenoid pin core 326 via the lever 264 and the spring 328. Should the $CO_2$ paintball 266 pin be closed, before the solenoid pin core 326 has reached its end position, the spring 328 further expands opening the clamping jaws 330 which are pivotably connected to solenoid pin core 326, thus releasing pin 332 which is articulated at the end of the lever 264. It should be noted that the force of the spring 328 is smaller than the closing force of the $CO_2$ paintball 266 pin.

When the solenoid coil 322 is activated, the solenoid core pin 326 moves forward (i.e. to the left in FIG. 13B) and pushes the clamping jaws 330 into clamping engagement with the pin 332 in order to move the pin 332 together with solenoid pin core 326. Pin 332 pushes the lever arm 264, which in turn presses the paintball 266 in order to release the $CO_2$ gas.

Figure 14:
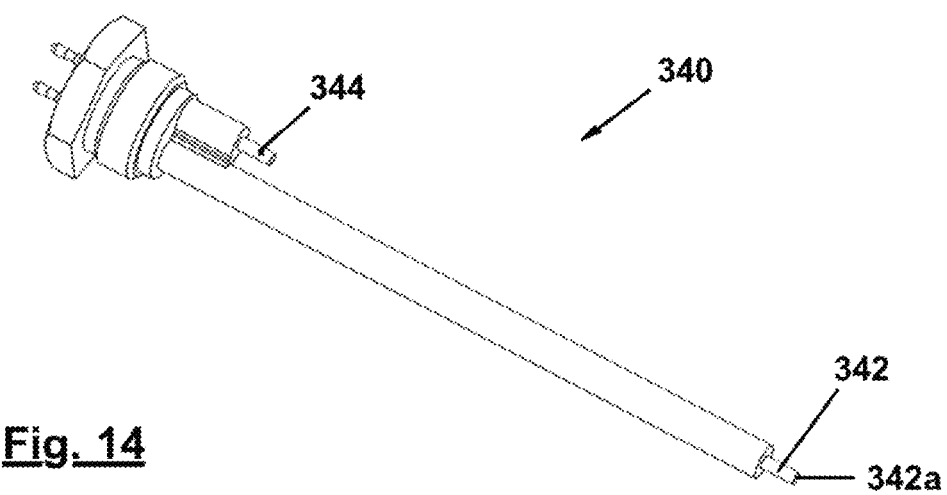
FIG. 14 shows a perspective view of the liquid level sensor unit according to the present invention.
Figures 15A, 15B:
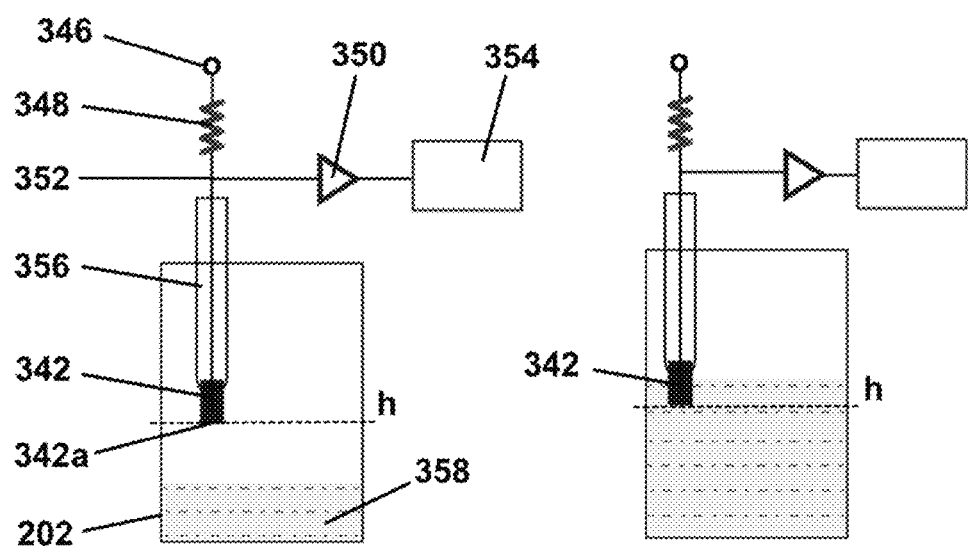
FIGS. 15A and 15B show the arrangement of the liquid level sensor in a situation, in which the liquid level is below the sensor height (FIG. 15A), and in a situation, in which the liquid level is above the sensor height (FIG. 15B) such that the liquid is in contact with the sensor tip.
Figures 16A, 16B:
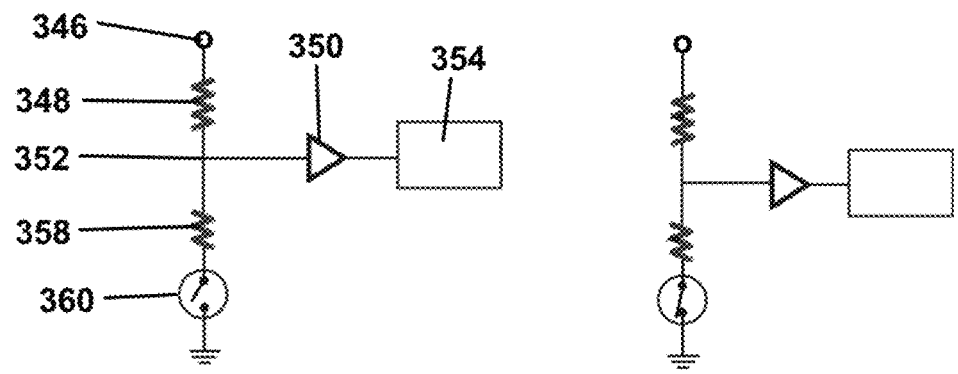
FIGS. 16A and 16B show the equivalent electrical circuits corresponding to FIGS. 15A and 15B, respectively.

FIG. 14 shows a perspective view of the liquid level sensor unit 340 according to the present invention. FIGS. 15A and 15B show the arrangement of the liquid level sensor 342 in a situation, in which the liquid level is below the sensor height h (FIG. 15A), and in a situation, in which the liquid level is above the sensor height h (FIG. 15B) such that the liquid is in contact with the sensor tip. And FIGS. 16A and 16b show the equivalent electrical circuits corresponding to FIGS. 15A and 15B, respectively.

The liquid level sensors 342, 344 of the liquid sensor unit 340 according to the invention are detecting the liquid height level in a new way based on the Ohm's low. Ohm's law states that the current flowing through a conductor between two points is directly proportional to the voltage across the two points. Mathematical equation that describes this relationship is:

$$V = R \cdot I$$

where I is the current in units of amperes, V is the voltage in units of volts and R is the resistance in units of ohms.

Existing liquid level sensors mostly rely on detecting the liquid by detecting the liquid's resistance, for example the resistance between two electrodes positioned in the liquid. The detecting of liquid based on resistance value may not present clear results, as the changes of the liquid's purity may cause uncertainty.

The sensor 342 proposed is based on an electrical circuit containing a power supply 346, a resistor 348, and a device 350 for detecting the voltage at a given point 352, i.e. to detect the voltage drop over the resistor 348. When the liquid is not in contact with the sensor tip 342a, the voltage sensed at the given point 352 is similar to the value V of the power supply voltage. However, when the sensor tip 342a is in contact with the liquid, and the liquid is grounded, for example by a grounded metal tank, a certain current will flow through the liquid and a drop in voltage will be sensed at the given point 352 due to the voltage drop over the resistor 348.

In particular, the sensor unit 340 according to the present invention comprises a conductive sensor tip 342a connected to a power supply 346 via an electrically conductive line and resistor 348 of fixed resistance R. A voltage detector 350 connected to a microcontroller unit 354 is attached to line at the given point 352 for analyzing the results sensed. An isolating housing 356 protects the electrical line which connects between the sensor tip 342a and the power supply 346. The sensor tip 342a is positioned in the vessel 202 at a height h required to be detected. The liquid 358 is connected to ground via the tank 202.

FIG. 15A and the corresponding electrical circuit shown in FIG. 16A represent a situation in which the sensor tip 342a is not in contact with the liquid. Accordingly, the switch 360 of the electrical circuit of FIG. 16A is open. As a consequence, there is no flow of current over the resistor 348, the voltage drop ΔV over the resistor 348 is 0, and the voltage sensed at point 352 is the voltage V provided by the power supply 346.

FIG. 15B and the corresponding electrical circuit shown in FIG. 16B represent a situation in which the sensor tip 342a is in contact with the liquid, e.g. water. As water normally is conductive, unless purified to highest level, the switch 360 of the electrical circuit of FIG. 16B is closed. As a consequence, there is a flow of current over the resistor 348 causing a voltage drop ΔV over the resistor 348.

$$\Delta V = V \cdot R / (R+r)$$

V designating the voltage provided by the power supply 346, R designating the resistance of the resistor 348, and r designating the resistance of the water 358.

If the resistance R of the resistor 348 is selected to be substantially equal to the resistance R of the water (R=r), the voltage drop ΔV over the resistor will be about half of the voltage V provided by the power supply 346 (ΔV=½ V).

Figure 17:
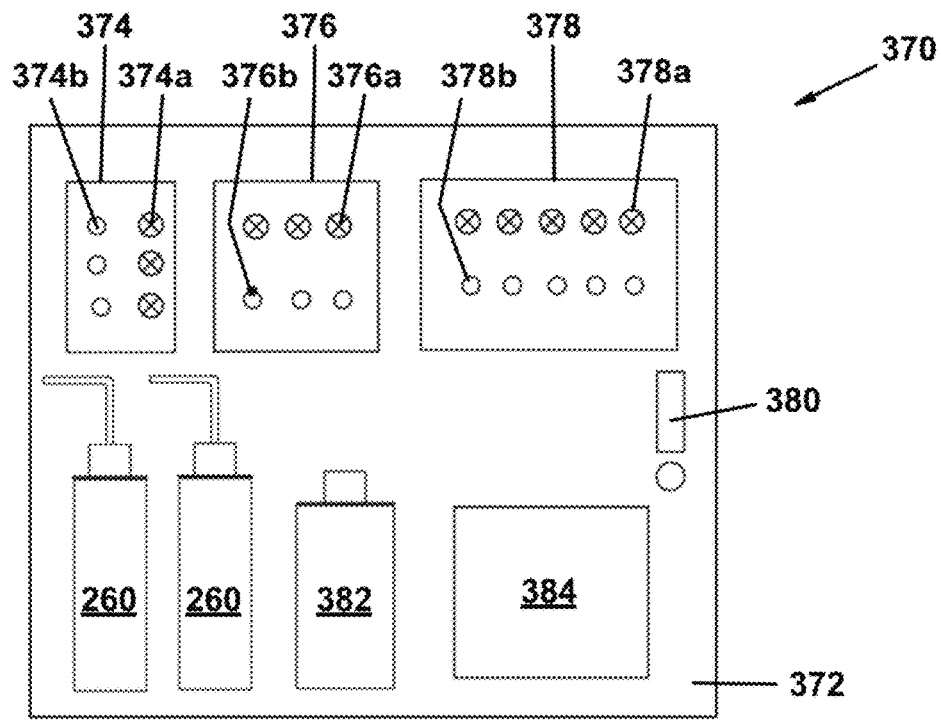
FIG. 17 shows a schematic view of a manifold according to the present invention.

FIG. 17 shows a schematic view of a manifold 370 according to the present invention.

The manifold 370 proposed intends to control and dispatch the chosen liquid to the faucet 112 and to hold as many components as required for the operation of the system 100. Since the number of liquids, which may be used, is large, the manifold 370 is flexible to be adopted for using a changing variety of liquids.

In addition to its basic purpose to handle the liquid flow in and out, by an organized pipe arrangement with solenoids to control the flow of the different type of water-based liquids out to the faucet, the manifold 370 proposed is flexible to a wide variety of liquids, handling safety components, such as safety group, pressure sensor, pressure relief valve, and consumable parts, such as $CO_2$ canister, additive materials, filters, sterilizer UV lamp and the like.

The manifold 370 comprises a housing box 372, preferably made from mold-injected plastics, having with inlet and outlet pipes, internal liquid paths, controlled by solenoids assembled on the box in the right places, to manage the distribution of the liquids.

The expandable manifold 370 consists of few boards, such as boards 374, 376, and 378 in FIG. 17. Each of the boards may contain a few ingoing pipes 374a, 376a, and 378a and a few outgoing pipes 374b, 376b, and 378b controlled by solenoid valves, to control the flow of the liquids. A safety group 380 may be added when the system contains a boiler. The manifold 370 may include consumable parts like $CO_2$ cylinders 260, additive containers 382 for enriching the water, such as syrup, flavors drops, minerals, coffee, etc., water filter and water treatment device 384 such as UV light sterilizer.

Figure 18:
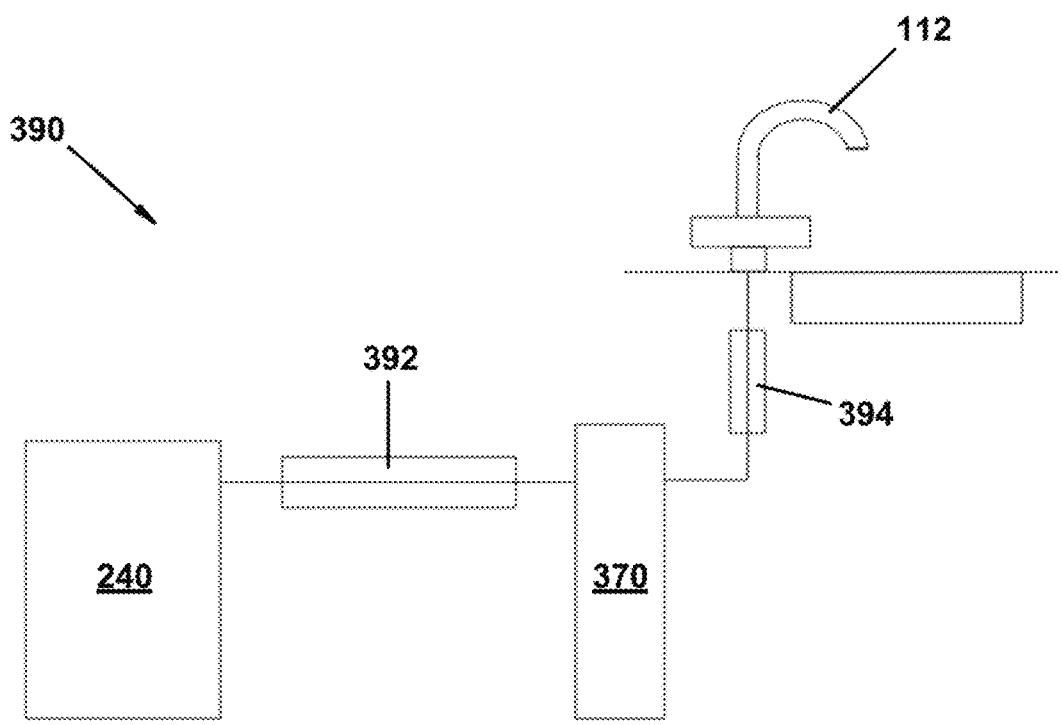
FIG. 18 shows possible locations for arranging a water sterilizing unit.

FIG. 18 shows possible locations for arranging a water sterilizing unit 390.

Water sterilizing devices 392, 394 may be positioned either between tank 240, i.e. the source of the supplied water, and manifold 370 or alternatively between the manifold 370 and the faucet 112.

Each of the water sterilizing units 392, 394 comprises a pipe and an internal UV light source to treat the water coming out of the tank 240. The pipe is integrated in the water-based liquid supply system 100 and turned on selectively when sterilizing is required. An alternative arrangement comprises a transparent pipe and an external UV light source.

Figure 19:
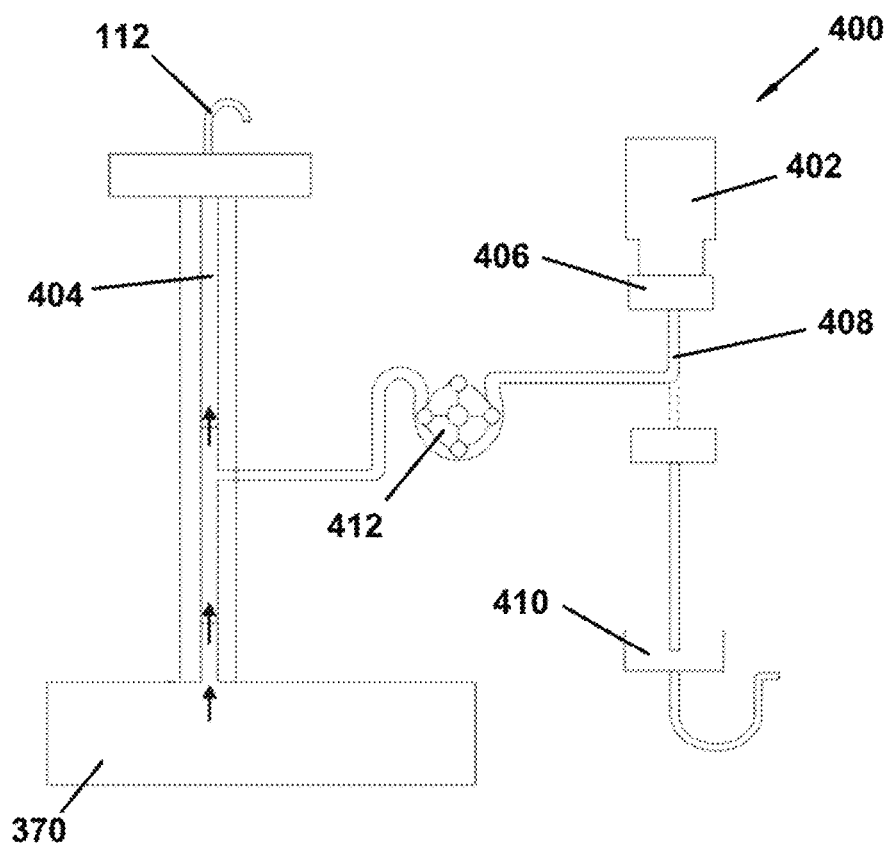
FIG. 19 shows a schematic view of a flavor unit according to the present invention.

FIG. 19 shows a schematic view of a flavor unit 400 according to the present invention.

The flavor unit 400 proposed provides the option to inject additives to the water-based liquid. Such additives may be water flavor, vitamins, minerals etc. The system may comprise a container 402 filled with any additive. The container 402 may be connected to the pipe 404 which is holding the water flow from the source, e.g. from the manifold 370, to the faucet 112. The connection includes a mixing injection chamber 406. The flavor unit 400 further includes the option to wash the pipe 408 connecting the container 402 to the mixing injection chamber 406. The pipe 408 may be connected to the drain 410, and by circulating the pump 412 in opposite direction the water-based liquid (for example boiling water) may be frowned from pipe 404 to the drain 410 through pipe 408 and clean it.

According to another aspect, the present invention further relates to a control unit 500 for controlling, in general, kitchen smart home appliances, such as the water-based liquid supply system 100 according to the present invention, a cooker 502, a hood 504, or other IOT devices 506, 508, such as a refrigerator, an oven, a microwave, a dish washer and other devices installed in the kitchen, but also other smart home appliances. In the following, the description will, only for the purpose of illustration, concentrate on the control of the water-based liquid supply system 100, the cooker 502 and the kitchen hood 504. It is, however, not intended to thereby limit the scope of invention. The use of the control system 500 according to the present invention for controlling the home appliances, the such as the water-based liquid supply system 100, the cooker 502 and the hood 504, provides a wide range of capabilities.

For example, the use of the control system 500 combined with the water-based liquid supply system 100 provides the following advantages:

It expands the selection options of the water-based liquids for drinking and cooking. For example, controlling the process of the under-sink machines, and controlling mixing liquids (fluids) provide the option of the selecting the temperature and concentration of the liquid dispatched. For example, temperature control is desired, as the preferred temperature for preparing tea is 80° C., while the preferred temperature for cooking pasta is 100° C. Furthermore, concentration control is required when mixing water or soda, with syrup, as different syrup concentrations may be required for different users. Another example would be soda mixing with water for controlling of soda strength.

It makes the use of the water-based liquid supply system 100 user-friendly and comfortable. A communication device 510 combined to the control system 500 allows the user to control and operate the water-based liquid supply system 100 from a smart mobile device 512, both indoors and outdoors, e.g. by using voice commands input via a voice recognition device 514.

It expands the services capabilities. For example, the control system 500 may calculate the use of consumables and output alerts for the need of replacement of filters, $CO_2$ cylinders 260 and the like ahead of time, e.g. together with providing a direct link to service providers for purchasing parts or apply for services.

It provides a dashboard presenting the performance and history of usage of the system, allowing the user to improve the efficiency of the system and energy saving.

It increases the safety in use, as it provides a higher safety in operation, for example remote locking of devices. For example a boiling water locker may remotely shut off the cooker left on. Priority in energy consumption may be set when reaching the limits of usage.

It improves health aspects by replacing filters on time and by operating a self-cleaning cycle. The control unit 500 acts periodically to wash pipes and containers in the system using boiled water heated in the boiler to prevent bacterial growth and viruses.

The communication system 510 allows every sub-system to monitor and control every other sub-system, excluding intentionally prevented access due to safety, security and operational aspects. A sub-system may be provided as an IOT device, smartphone app, control panel, speech recognition device, cloud as well as devices through cloud.

The system offers two optional structures.
a) Direct app-IOT device architecture without using a cloud, and
b) IOT device/application-local hub-cloud-web-hub-IOT device/service,
and provides many advantages and options, such as:
remote upgrade of hub/devices software and firmware,
personal auto application detection of user location (indoors/outdoors), with no violation whatsoever of privacy,
automatic/manual adaption of parameters based on auto learning,
filtered alerts for errors, service needs, replacement need for consumable parts,
dashboard: behavior, distribution, energy.

The control system 500 offers many operational options such as:
setting and operation of parameters, timers, process and the like, both, indoors and outdoors,
setting of demands, such as water at a desired temperature, type of drink required at a desired temperature, concentration and the like,
remote, i.e. outdoors connectivity for controlling the system and updates,
providing and storing data from the system on a cloud for analysis, statistics etc., storing data for dashboards to visually see the system performances,
establishing a communication channel with a third party for providing services,
following and observing the status of the system parts, such as a compressor, heaters etc., to provide alerts or service when required, or offering the supply of consumable parts when needed, such as filters and $CO_2$ refilled containers or syrup.

Figure 20C:
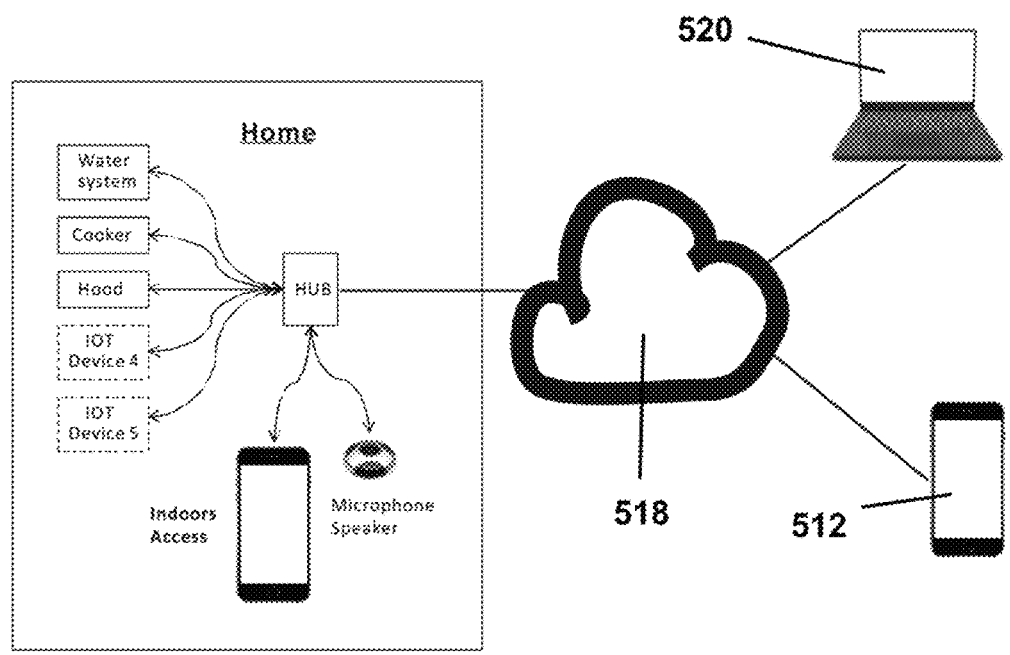
FIG. 20C is a schematic arrangement of the control system and its communication system for the kitchen appliances with outdoor communication.
Figure 20B:
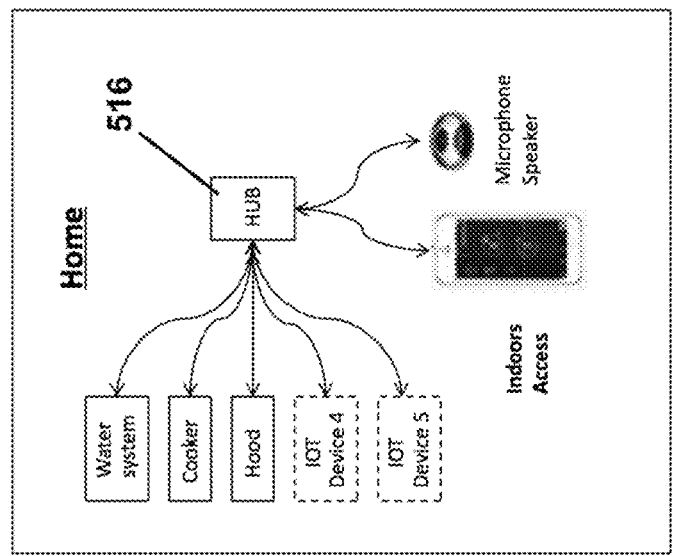
FIG. 20B is a schematic indoor arrangement of the control system and its communication system for the kitchen appliances including a hub and application control.
Figure 20A:
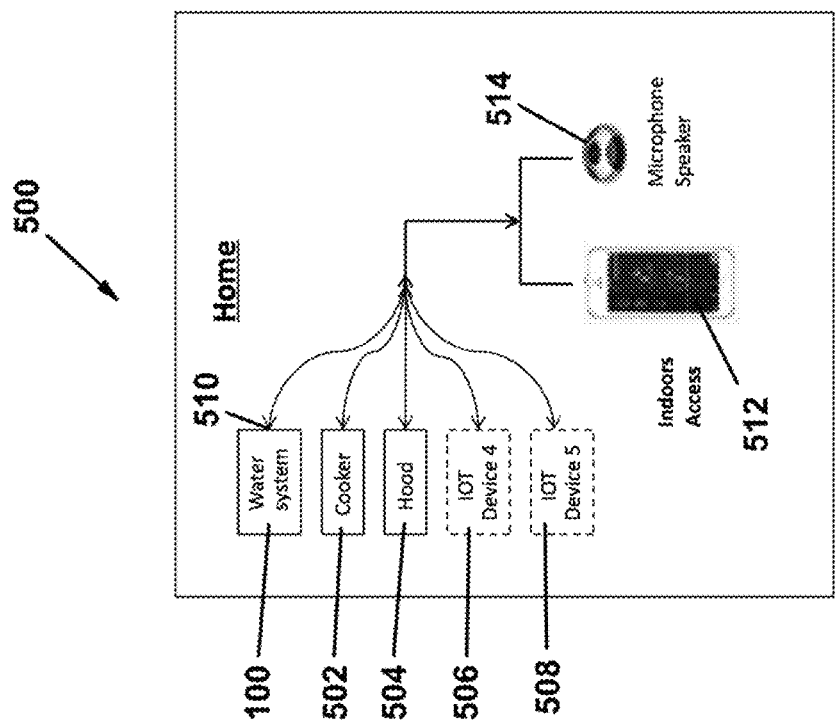
FIG. 20A is a schematic indoor arrangement of the control system and its communication system for the kitchen appliances without a hub.

FIG. 20A is a schematic indoor arrangement of the control system 500 and its communication system 510 for the kitchen appliances without a hub.

FIG. 20B is a schematic indoor arrangement of the control system 500 and its communication system 510 for the kitchen appliances including a hub 516 and application control.

FIG. 20C is a schematic arrangement of the control system 500 and its communication system 510 for the kitchen appliances with outdoor communication. In particular, FIG. 20C represents a detailed chart including an indoor hub 516, a cloud connection 518, in particular for providing an outdoor virtual hub, and the smart mobile device 512, 520. Optional applications may be video camera devices control system, boot loader, speech recognition, indoor applications connected to the local hub by Bluetooth, and the local hub which is contact with the virtual hub in the cloud. The cloud option opens a wide range of applications, such as availability of data bases, both public and private applications and web personal assistance. The cloud web applications include dashboards service and store, white labelling, monitoring and alerts.

Figure 21:
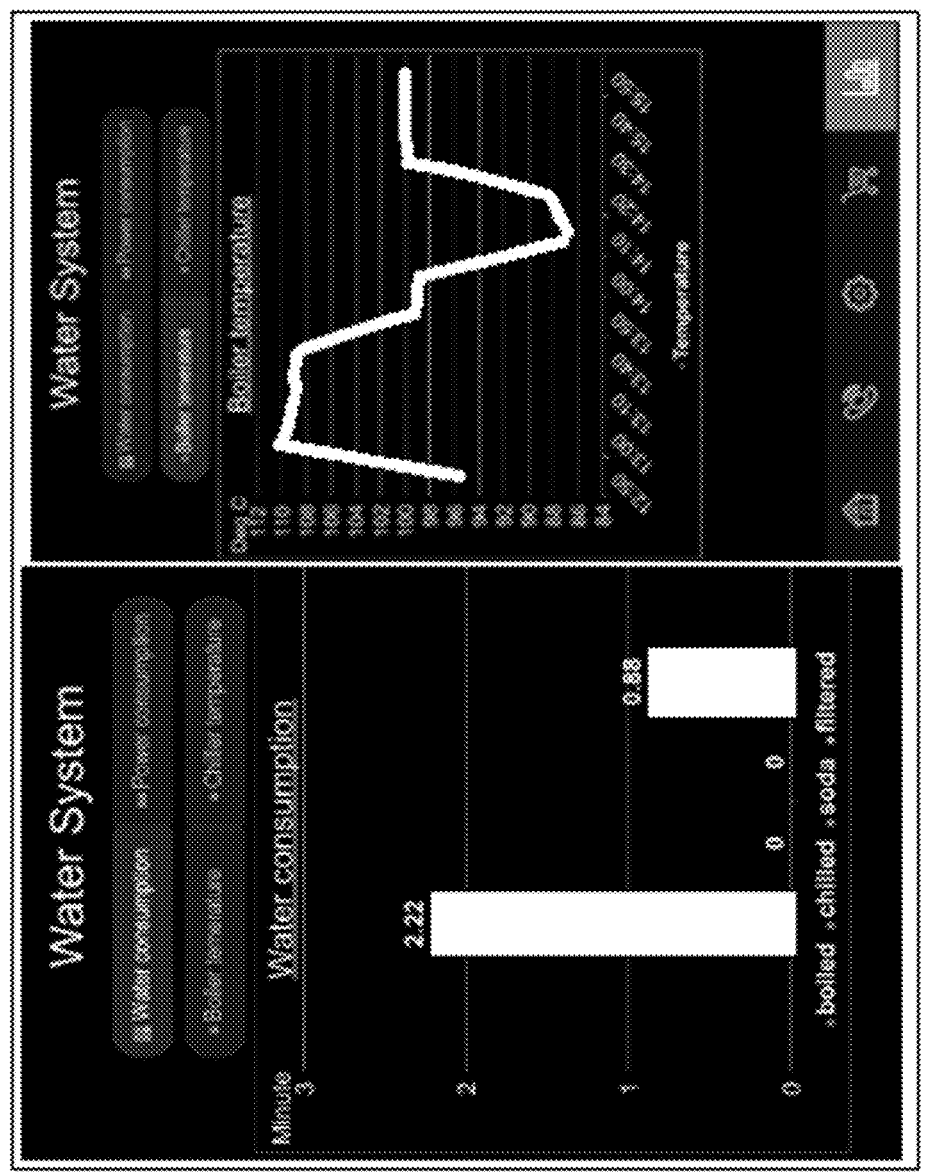
FIG. 21 shows an example of the dashboard generated by the smartphone application to demonstrate the data collected on "water consumption" and "boiler temperature" from the system.

FIG. 21 shows an example of the dashboard generated by the smartphone application to demonstrate the data collected on "water consumption" and "boiler temperature" from the system.

In the following, a detailed description of the control system 500 and its communication system 510 will be given.

In particular, an upgradable control system 500 for IOT solution is provided, including optional utilization levels of the control system 500 of the IOT solution (1) local, proprietary control panels controlling kitchen devices directly using wired or wireless communication, (2) smartphones 520 with proprietary applications controlling kitchen devices directly using wireless communication, (3) smartphones 520 (or other control devices described on utilization level (3)) controlling kitchen devices indirectly using wireless communication through a hub 516, i.e. a local gateway;

(4) smartphones 520 (or other control devices described on utilization level (4)) controlling kitchen devices indirectly using wireless communication through a cloud 518, i.e. global internet and hub, (5) smartphones display of performance, real time reporting (dashboard) as well as real time notification (alert), call center (CRM) interfaces for sales and support.

Utilization Level (1) —Proprietary Control Units:

Utilization level (1) refers to the applicant's kitchen devices, which may be controlled by the applicant's proprietary control units. Control units may control/display/communicate with one or more kitchen device(s) simultaneously, and may enable direct connection among kitchen devices themselves. The connection of the control units to the kitchen devices may be wired or wireless (IR, RF (i.e. ZigBee/BLE/Wi-Fi/))

Utilization Level (2) —Smartphone:

In addition to or instead of the proprietary control units, the user may prefer to operate his kitchen devices through his smartphone 520. All of the applicant's devices support the connection to wireless smartphone communication, and give the user a very user-friendly, feature-rich real-time opportunity to control his kitchen devices.

Utilization Level (3) —Local Hub:

Instead of a direct connection of a smartphone 520 to the kitchen devices the user may prefer to add a hub 516 which enables
- smartphone control of all kitchen devices (similar to direct connection as in utilization level (1)),
- local speech recognition control,
- local gesture control,
- interface with other local sub-systems/sensors/indications,
- interface with other local IOT systems/vendors,
- cloud interface (internet) described in utilization levels (4) and (5)

Utilization level (4) —Internet (Cloud) Control:

In the same way the applicant's smartphone applications can connect to the applicant's kitchen devices indoors both, directly or indirectly through a hub 516. It can also connect outdoors through the applicant's cloud infrastructure.

Similarly to the hub 516, the applicant's cloud solution is not just limited to smartphone control, it also enables
- voice control via a speech recognition service, e.g. Amazon Alexa or Google Home,
- gesture control,
- control by other sub-systems/sensors,
- control by other IOT solution makers.

Utilization Level (5) —Internet (Cloud) Display/Alert/Services:

The cloud connectivity may be bidirectional and used not only for control (incoming communication), it enables also outgoing communication for the following purposes:
- real time graphical historical reporting of usage of resources, and other parameters important for the user to know (dashboard),
- immediate alerts to the user's smartphone on issues that may be urgent and important to the user, i.e. issues related to safety, need for replacement of consumables etc.,
- interface with various kinds of internet services, call center CRM software solutions, consumables webstore services etc.

Additional points:
- dispatching a water-based liquid at a desired temperature by mixing liquids from two sources of liquids having different temperatures.
- A new method for controlling the temperature of the liquid dispatched by mixing with water at a different temperature. The method is implemented whenever a liquid at a high temperature is mixed with water or a water-based liquid at lower temperature. When the system requires for example water at 55° C., a possible option is to mix for example boiling water at 100° C. which exists in the boiler of the system with chilled water from the chiller for example at 10° C. in equal portions and get the required 55° C. A more energy efficient method, however, may be a mix with purified water from the main water line. For this purpose, the water temperature of the main water line may be detected and recorded. The temperature of the main water line may, for example, be detected by measuring the drop of the boiler temperature when filling with water from the main water line.

Summary of Claimed Items

Item 1: A liquid supply system (100) for preparing and dispensing water-based liquids at a desired temperature and/or with at least one additive at a desired concentration on demand, the liquid supply system comprising:
- a water supply comprising at least one water tank (102) and/or a connection (130, 132) to a water main line,
- at least one faucet (112) having an outlet for dispensing the prepared water-based liquid, and
- at least three of the following additional devices:
  - a water filter adapted to filter water from the water supply,
  - a water boiler adapted to heat water from the water supply to a predetermined temperature,
  - a water chiller (302) adapted to cool water from the water supply to a predetermined temperature,
  - a soda machine (200) adapted to carbonize water from the water supply to a predetermined $CO_2$ concentration, and
  - an additive mixer (129) adapted to mix at least one additive supplied from at least one additive container (126) at a predetermined concentration to water from the water supply;
- the liquid supply system (100) further comprising
  - a piping system (107) connecting the water supply, the faucet (112) and the at least three additional devices installed in the liquid supply system, and
  - a communication and control system (500) adapted to communicate with a user and to control the preparation and dispensing of the water-based liquid based on a communication with the user.

Item 2: The liquid supply system according to item 1, wherein at least a part of the piping system (107) is adapted to be drained and/or to be flushed with a cleaning liquid, preferably boiling water, regularly or on demand or at predetermined occasions, such as a change in the kind of water-based liquid selected by the user.

Item 3: The liquid supply system according to item 1 or 2, wherein several components of the liquid supply system (100), such as the faucet (112), the water supply, one or several of the additional devices installed in the liquid supply system, the piping system (107) or parts of the piping system, are smart appliances adapted to communicate with each other and/or with the user and/or the outside world via the communication and control system (500), and wherein the communication and control system (500) is adapted to be accessed by the user via a local, proprietary control panel and/or via a mobile device such as a smartphone or tablet computer with a suitable mobile app, and wherein the communication and control system (500) is adapted to be accessed by the user directly and/or via a local hub or via cloud communication through the internet.

Item 4: The liquid supply system according to any of the preceding items, wherein the communication and control system (500) is adapted to monitor the consumption of at least one consumable part of the system such as a water filter and is preferably furthermore adapted to calculate an expected service life of the at least one consumable part taking into consideration the monitored consumption, and preferably at least one other influencing parameter, such as water quality, in particular water hardness, and/or ambient temperature.

Item 5: The liquid supply system according to any of the preceding items, furthermore comprising an expandable manifold (106) having at least one exchangeable board, each board comprising at least one ingoing pipe, preferably a plurality of ingoing pipes, and at least one outgoing pipe, preferably a plurality of outgoing pipes.

Item 6: The liquid supply system according to any of the preceding items, furthermore comprising a water tank connected to the water main line and adapted to store water at a predetermined temperature, wherein the liquid supply system is adapted to calculate a temperature of water in the water main line based on a quantity of water stored at the predetermined temperature in the water tank at a given time, a quantity of line water additionally filled into the tank and the resulting temperature difference of the water in the water tank.

Item 7: The liquid supply system according to any of the preceding items, wherein the liquid supply system (100) is adapted to prepare a predetermined number of different kinds of water-based liquids, each of these different kinds of water-based liquids being associated with a specific predetermined indication, e.g. with a specific predetermined color, and wherein the liquid supply system (100), preferably the faucet (112), comprises a display device, preferably located on the fixed base of the faucet, adapted to display the specific predetermined indication associated with the kind of water-based liquid that is currently being selected, prepared or dispensed.

Item 8: The liquid supply system according to any of the preceding items, furthermore comprising
- a selector knob (164) for selecting the desired kind of water-based liquid, the selector knob (164) comprising an outer shell (172) being adapted for, preferably bidirectional, rotation around an axis (A) in predefined steps with respect to a fixed part (134), e.g. of the faucet (112),
- a reflecting element (170) provided on one part, namely the outer shell (172) or the fixed part (134),
- an illuminating element (174) provided on the respective other part, namely the fixed part (134) or the outer shell (172), and adapted to illuminate the reflecting element (170), and
- an optical sensor device (178) provided on the respective other part, and adapted to detect the intensity of light reflected from the reflecting element (170) so that a rotation of the outer shell (172) by one step is detected by a change of the intensity of light reflected from the reflecting element (170), while the selector knob (164) is in a stationary condition.

Item 9: The liquid supply system according to item 8, wherein the reflecting element (170) is a reflector ring or a reflector disk divided in n sectors of equal form and size having alternatingly high and low reflectivity, n being a natural even number, and each sector covering an circumferential angle of 360°/n around the axis (A), and wherein the sensor device (178) comprises two sensor elements (178a, 178b) arranged in a circumferential distance of 180°/n.

Item 10: The liquid supply system according to any of the preceding items, comprising a soda machine (200) adapted to carbonize water from the water supply to a predetermined $CO_2$ concentration, the soda machine (200) comprising:
- a $CO_2$ container (160) containing $CO_2$ at a $CO_2$ container pressure, e.g. a pressure of 60 bar at 22° C.,
- a soda tank (202) connected to the water supply and to the $CO_2$ container, the connection between the $CO_2$ container and the soda tank being free of a pressure reducer,
- a $CO_2$ release mechanism (268) for releasing and injecting $CO_2$ gas from the $CO_2$ container (160) directly into the soda tank (202) through a nozzle (220) located in the soda tank, and
- a check valve installed in the line connecting the $CO_2$ container and the soda tank and preventing $CO_2$ gas from flowing back from the soda tank (202) to the $CO_2$ container (260).

Item 11: The liquid supply system according to item 10, wherein the water supply comprises a separate tank (240) for storing chilled water, the soda tank (202) being partially submerged in the separate tank (240), and wherein the soda tank (202) and the separate tank (240) are each provided with cooling coils (304, 306) for direct cooling.

Item 12: The liquid supply system according to item 10 or 11, wherein the soda machine (200) furthermore comprises an auxiliary $CO_2$ circulation system (280) comprising an expansion tank (284), a pipe (282) connecting the expansion tank (284) to the soda tank (202) via a pressure relief valve (286) that opens when the pressure in the soda tank (202) and the pipe (282) exceeds a preset pressure (p1) and a further pipe (288) connecting the expansion tank (284) to the soda tank (202) via a one-directional valve (290) blocking a flow of $CO_2$ gas and water or water droplets from the soda tank (202) to the expansion tank (284).

Item 13: The liquid supply system according to any of items 10 to 12, wherein the $CO_2$ release mechanism furthermore comprises a gap reducing mechanism adapted to reduce a backlash between components of the $CO_2$ release mechanism and the $CO_2$ container due to accumulated engineering tolerances of these components and/or due to changes in the mounting position of the $CO_2$ container when the $CO_2$ container is exchanged.

Item 14: The liquid supply system according to item 13, wherein the $CO_2$ release mechanism (268) furthermore comprises
- a lever mechanism (264, 332) for opening the $CO_2$ container (260) against the closing force of a container closing valve (266), and
- an actuator (262) with a movable actuator part (326) adapted to move between an activated position (FIG. 13A) and a non-activated position (FIG. 13B), the gap reducing mechanism furthermore comprising
- a spring (328) coupled between the lever mechanism (264, 332) and the movable actuator part (326) and biasing the movable actuator part (326) toward the non-activated position (FIG. 13A) and
- at least one clamping element (330) pivotably connected to the movable actuator part (326) and being displaceable between a clamping position, in which it is in clamping engagement with the lever mechanism (264, 332), and a release position, in which the lever mechanism (264, 332) may freely move relative to the movable actuator part (326), a movement of the movable actuator part (326) from its activated position (FIG. 13A) to its non-activated position (FIG. 13B) displacing the at least one clamping element (330) towards its release position.

Item 15: The liquid supply system according to any of the preceding items, comprising a liquid level sensor unit (340) provided in a water tank (202), said water tank (202) being made from a conductive material and being connected to ground, the liquid level sensor unit (340) comprising:
- a power supply (346) providing a predetermined voltage ($V_1$),
- a conductive sensor tip (342a) provided at a predetermined height (h) over a bottom of the water tank (202), the sensor tip (342a) being electrically connected to the power supply (346) via a resistor (348), and a device (350) for detecting a voltage at a predetermined point between the resistor (348) and the sensor tip (342a).

Item 16: A faucet, in particular as a part of a water-based liquid supply system according to any of items 1 to 15, said faucet comprising at least two internal conduits, preferably coaxial internal conduits, the internal conduits being separated, and preferably also thermally insulated, from each other.

Item 17: The faucet according to item 16, wherein one of the internal conduits is an inner conduit arranged within the other internal conduit, the inner conduit being further divided internally into at least two internal ducts which are separated, and preferably also thermally insulated, from each other.

Item 18: The faucet according to item 17, wherein the inner conduit is thermally insulated in the faucet from an entry point to an outlet to prevent heat transfer between the liquid and the faucet.

Item 19: The faucet according to any of items 16 to 18, comprising a fixed faucet base and a swiveling spout, wherein the at least two internal conduits are arranged coaxially and have a circular cross-section at least in a region in which the swiveling spout is connected to the fixed faucet base.

Item 20: The faucet according to any of items 16 to 18, comprising a fixed faucet base and a swiveling spout, wherein for at least one of the internal conduits, a flexible pipe is inserted in the spout or part of it, the flexible pipe connecting the respective internal conduit in the swiveling spout with a pipe extending in the faucet base.

Item 21: The faucet according to any of items 16 to 20, comprising a selector device such as a knob or a control panel designed to select a water-based liquid from a predetermined number of different kinds of water-based liquids, each of these different kinds of water-based liquids being associated with a different predetermined indication, e.g. color, and wherein the faucet furthermore comprises a display device adapted to display the specific predetermined indication associated with the kind of water-based liquid that is currently being selected, prepared or dispensed.

Item 22: The faucet according to item 21, comprising a selector device, preferably a knob or a lever, for selecting the desired type of liquid, wherein the selector device is adapted to be rotated around an axis in predefined steps synchronized with the display device, and wherein the faucet preferably furthermore comprises a detector device for detecting a current rotational position of the selector device.

Item 23: The faucet according to item 22, wherein the selector device is illuminated and comprises at least two optical sensor elements positioned at a predetermined location and at a predetermined angular distance from each other in order to detect light reflected by the selector device.

Item 24: The faucet according to any of items 16 to 23, furthermore comprising a selector knob for selecting the desired kind of water-based liquid, the selector knob comprising an outer shell being adapted for, preferably bidirectional, rotation around an axis in predefined steps with respect to a fixed part, e.g. of the faucet, a reflecting element provided on one part, namely the outer shell or the fixed part, an illuminating element provided on the respective other part, namely the fixed part or the outer shell, and adapted to illuminate the reflecting element, and an optical sensor device provided on the respective other part, and adapted to detect the intensity of light reflected from the reflecting element so that a rotation of the outer shell by one step is detected by a change of the intensity of light reflected from the reflecting element.

Item 25: The faucet according to item 24, wherein the reflecting element is a reflector ring or a reflector disk divided in n sectors of equal size and having alternatingly high and low reflectivity, n being a natural even number and each sector covering an circumferential angle of 360°/n, and wherein the sensor device comprises two sensor elements arranged in a circumferential distance of 180°/n.

Item 26: A soda machine, in particular as a part of a water-based liquid supply system according to any of items 1 to 15, said soda machine comprising:

a $CO_2$ container containing $CO_2$ at a $CO_2$ container pressure, e.g. 60 bar at 22° C., a soda tank connected to the water supply and to the $CO_2$ container, the connection between the $CO_2$ container and the soda tank being free of a pressure reducer, a $CO_2$ release mechanism for releasing and injecting $CO_2$ gas from the $CO_2$ container directly into the soda tank through a nozzle located in the soda tank, the $CO_2$ release mechanism preferably comprising a lever mechanism for opening the $CO_2$ container and an actuator, in particular an electrical actuator, such as a solenoid actuator or an electrical motor, for operating the lever mechanism, and a check valve installed in the line connecting the $CO_2$ container and the soda tank and preventing $CO_2$ gas from flowing back from the soda tank to the $CO_2$ container.

Item 27: The soda machine according to item 26 for preparing soda by mixing $CO_2$ in a predetermined amount of water for delivering continually one or more cups of carbonated water mixed with plain water and/or other additives.

Item 28: The soda machine according to item 26 or 27, wherein an operating process for preparing soda or part of said operating process, e.g., $CO_2$ gas injection, is an automatic operating process that is interruptible at any time and replaceable by manual commands.

Item 29: The soda machine according to any of items 26 to 28, furthermore comprising a cooling system adapted to keep the soda tank cooled to a predetermined temperature or temperature range for storing and consumption at any time.

Item 30: The soda machine according to any of items 26 to 29, wherein the soda tank comprises an air trap at the top of the tank to limit the highest water level, wherein an upper water level and a lower water level may be detected by corresponding sensors, respectively, or alternatively be controlled by a software application controlling a water filling process by a timer and calculating whether the corresponding water lever has been reached based on an amount of soda consumed or water filled in, respectively.

Item 31: The soda machine according to any of items 26 to 30,
adapted to control a $CO_2$ concentration by a controller with or without a software application,
controlling soda preparation parameters, such as an amount of $CO_2$ injected, an injection pattern of the injected $CO_2$ gas, a pressure held in the soda tank while injecting the $CO_2$.

Item 32: The soda machine according to any of items 26 to 31,
furthermore comprising a pressure sensor in communication with the soda tank to limit the maximum pressure allowed in the tank and/or to influence the $CO_2$ injection amount and/or to influence the soda intensity and/or to detect low pressure and inject additional amount of $CO_2$ gas for keeping the required pressure in the tank and/or to detect after injection the need to replace the empty $CO_2$ container.

Item 33: The soda machine according to any of items 26 to 32,
furthermore comprising a Bluetooth and/or WiFi connection for remote controlling and operating and/or for communicating with other smart appliances and/or for providing cloud services, such as maintenance and/or supply of consumable parts.

Item 34: The soda machine according to any of items 26 to 33,
furthermore comprising a separate tank for storing chilled water, the soda tank being submerged partially in the separate tank, and wherein the soda tank and the separate tank are each provided with cooling coils for direct cooling.

Item 35: The soda machine according to any of items 26 to 34,
furthermore comprising a separate tank for storing chilled water, the separate tank having a connection for a water main line and wherein water main line is adapted to refill the water tank automatically whenever water flows out of the water tank, e.g. to the faucet or to the soda tank.

Item 36: The soda machine according to any of items 26 to 35,
furthermore comprising a relief pipe with a controllable solenoid valve adapted to release the pressure from the soda tank when required, for example, during the filling of the soda tank with water or whenever required for soda preparation.

Item 37: The soda machine according to item 36,
wherein an inlet of the relief pipe is positioned in the soda tank at a predetermined height below the top level to create an air trap at the top of the tank, preventing the water from occupying the full volume of the tank and securing free space for $CO_2$ injected into the tank.

Item 38: The soda machine according to any of items 26 to 37,
furthermore comprising an auxiliary $CO_2$ circulation system for keeping undissolved $CO_2$ injected to the soda tank, and returning it back to the soda tank, when the pressure in the soda tank drops, for maintaining a desired controlled pressure in the soda tank, and for preventing the need to handle water drops flushed together with the $CO_2$ gas exhausted, the auxiliary $CO_2$ circulation system preferably comprising an expansion tank, a pipe connecting the expansion tank to the soda tank via a pressure relief valve that opens when the pressure in the soda tank and the pipe exceeds a preset pressure and a further pipe connecting the expansion tank to the soda tank via a one-directional valve balancing the pressure between the expansion tank and the soda tank.

Item 39: The soda machine according to any of items 26 to 38,
furthermore comprising a $CO_2$ container magazine for holding a plurality of $CO_2$ containers, the soda machine being preferably adapted to control the soda preparation in such a manner that the $CO_2$ container currently used for injecting $CO_2$ is automatically replaced by a full one from the magazine when the pressure in the currently used $CO_2$ container drops below a preset threshold.

Item 40: The soda machine according to item 39,
wherein the soda machine is adapted to monitor the current number of full $CO_2$ containers in the magazine and to output a warning when this number drops below a preset threshold.

Item 41: The soda machine according to any of items 26 to 40,
wherein the $CO_2$ release mechanism furthermore comprises a gap reducing mechanism adapted to reduce a backlash between components of the $CO_2$ release mechanism and the $CO_2$ container due to accumulated engineering tolerances of these components and/or due to changes in the mounting position of the $CO_2$ container when the $CO_2$ container is exchanged.

Item 42: The soda machine according to item 41,
wherein the $CO_2$ release mechanism furthermore comprises
a lever mechanism for opening the $CO_2$ container against the closing force of a container closing valve, and
an actuator with a movable actuator part adapted to move between an activated position and a non-activated position,
the gap reducing mechanism furthermore comprising
a spring coupled between the lever mechanism and the movable actuator part and biasing the movable actuator part toward the non-activated position and
at least one clamping element pivotably connected to the movable actuator part and being displaceable between a clamping position, in which it is in clamping engagement with the lever mechanism, and a release position, in which the lever mechanism may freely move relative to the movable actuator part, a movement of the movable actuator part from its activated position to its non-activated position displacing the at least one clamping element towards its release position.

Item 43: A liquid level sensor, in particular as a part of a water-based liquid supply system according to any of items 1 to 15, said liquid level sensor comprising at least one electrode powered by an electrical voltage supply, the liquid sensor being adapted to detect an electrically conductive liquid connected to ground, preferably by a grounded tank, when the liquid enters into contact with the sensor.

Item 44: The liquid level sensor according to item 43,
comprising a resistor and an electrical circuit connecting the electrical voltage supply to the sensor via the resistor, so that a voltage drop over the resistor changes whenever a grounded liquid enters into contact with the sensor.

Item 45: A UV sterilizing device, in particular as a part of a water-based liquid supply system according to any of items 1 to 15, said UV sterilizing device being adapted to sterilize a liquid in a tank or flowing through a pipe by irradiating it with UV light.

Item 46: The UV sterilizing device according to item 45,
the UV light sources being provided inside a tank or a pipe.

Item 47: The UV sterilizing device according to item 45,
the UV light sources being provided outside a tank or a pipe, said tank or pipe being at least locally transparent.

Item 48: A control and communication system, in particular as a part of a water-based liquid supply system according to any of items 1 to 15, said control and communication system being adapted to control at least one smart device, in particular at least one smart kitchen appliance, the control and communication system being adapted to connect the at least one smart devices with communication capability, e.g. a liquid supply system, a hood, a cooker or the like, in such a manner that the smart device can communicate with a user and/or in case of at least two smart devices with each other, preferably by wireless communication, using short distance communication technology for activating, programming, and controlling the system, e.g. zigbi, Bluetooth or an equivalent technology.

Item 49: The control and communication system according to item 48,
wherein the communication and control system is adapted to be accessed by the user via a local, proprietary control panel and/or via a mobile device, such as a smartphone or a tablet computer with a predetermined mobile app, for example by voice commands, and wherein the communication and control system is adapted to be accessed by the user directly and/or via a local hub and/or a local network and/or via cloud communication through the Internet.

Item 50: The control and communication system according to item 48 or 49,
comprising a local hub or a router adapted to allow the communication between each of the devices connected by the system through the local hub.

Item 51: The control and communication system according to item 50,
wherein the local hub connects the system to a cloud for remote setup and communication, to provide predetermined services, such as bidirectional data exchange and/or providing dashboards and/or allowing remote operation and/or push notifications and/or approach of service providers and/or support and/or store service options.

Item 52: The control and communication system according to any of items 48 to 51,
wherein the control and communication system is a cloud communication system having an indoor hub connecting indoor smart devices and a virtual hub held in the cloud for managing communication between external smart devices located outdoor, the indoor hub, the indoor smart devices and the user.

Item 53: The control and communication system unit according to item 52,
wherein the indoor hub is adapted to communicate with the virtual hub for providing the system with web server capabilities, such as web applications and/or web personal assistance and/or public and private databases and/or dashboards and/or push notifications and/or service and store and/or white labelling and/or monitoring and/or alerts.

The invention claimed is:

1. A liquid supply system for preparing and dispensing water-based liquids at a desired temperature and with at least one additive at a desired concentration on demand, the liquid supply system comprising:
a water supply comprising at least one water tank and/or a connection to a water main line;
at least one faucet having an outlet for dispensing the prepared water-based liquid;
a water filter adapted to filter water from the water supply;
at least one of a water boiler adapted to heat water from the water supply to a predetermined temperature or a water chiller adapted to cool water from the water supply to a predetermined temperature;
a soda machine adapted to carbonize water from the water supply to a predetermined concentration of $CO_2$ gas;
an additive mixer adapted to mix at least one additive supplied from at least one additive container at a predetermined concentration to water from the water supply, wherein the at least one additive is different from the $CO_2$ gas;
a piping system connecting the water supply, the faucet, the water filter, the soda machine, the additive mixer, and the at least one of the water boiler or the water chiller; and
a communication and control system adapted to communicate with a user and to control the preparation and dispensing of the water-based liquid based on a communication with the user.

2. The liquid supply system according to claim 1, wherein at least a part of the piping system is adapted to be drained and/or to be flushed with a cleaning liquid regularly or on demand or at predetermined occasions.

3. The liquid supply system according to claim 1, wherein several components of the liquid supply system, the water supply, one or several of the additional devices installed in the liquid supply system, the piping system or parts of the piping system, are smart appliances adapted to communicate with each other and/or with the user and/or the outside world via the communication and control system, and wherein the communication and control system is adapted to be accessed by the user via a local, proprietary control panel and/or via a mobile device, and wherein the communication and control system is adapted to be accessed by the user directly and/or via a local hub or via cloud communication through the internet.

4. The liquid supply system according to claim 1, wherein the communication and control system is adapted to monitor the consumption of at least one consumable part of the system.

5. The liquid supply system according to claim 1, further comprising an expandable manifold having at least one exchangeable board, each board comprising at least one ingoing pipe and at least one outgoing pipe.

6. The liquid supply system according to claim 1, further comprising a water tank connected to the water main line and adapted to store water at a predetermined temperature, wherein the liquid supply system is adapted to calculate a temperature of water in the water main line based on a quantity of water stored at the predetermined temperature in the water tank at a given time, a quantity of line water additionally filled into the tank and the resulting temperature difference of the water in the water tank.

7. The liquid supply system according to claim 1, wherein the liquid supply system is adapted to prepare a predetermined number of different kinds of water-based liquids, each of these different kinds of water-based liquids being associated with a specific predetermined indication, and wherein the liquid supply system comprises a display device adapted to display the specific predetermined indication associated with the kind of water-based liquid that is currently being selected, prepared or dispensed.

8. The liquid supply system according to claim 1, further comprising:
a selector knob for selecting the desired kind of water-based liquid, the selector knob comprising an outer shell being adapted for rotation around an axis in predefined steps with respect to a fixed part;
a reflecting element provided on one part, namely the outer shell or the fixed part;

an illuminating element provided on the respective other part, namely the fixed part or the outer shell, and adapted to illuminate the reflecting element; and an optical sensor device provided on the respective other part, and adapted to detect the intensity of light reflected from the reflecting element so that a rotation of the outer shell by one step is detected by a change of the intensity of light reflected from the reflecting element.

9. The liquid supply system according to claim 8, wherein the reflecting element is a reflector ring or a reflector disk divided in n sectors of equal form and size having alternatingly high and low reflectivity, n being a natural even number, and each sector covering an circumferential angle of 360°/n around the axis, and wherein the sensor device comprises two sensor elements arranged in a circumferential distance of 180°/n.

10. The liquid supply system according to claim 1, wherein the soda machine comprises:
a $CO_2$ container containing the $CO_2$ gas at a $CO_2$ container pressure;
a soda tank connected to the water supply and to the $CO_2$ container, the connection between the $CO_2$ container and the soda tank being free of a pressure reducer;
a $CO_2$ release mechanism for releasing and injecting the $CO_2$ gas from the $CO_2$ container directly into the soda tank through a nozzle located in the soda tank; and
a check valve installed in the line connecting the $CO_2$ container and the soda tank and preventing the $CO_2$ gas from flowing back from the soda tank to the $CO_2$ container.

11. The liquid supply system according to claim 10, wherein the water supply comprises a separate tank for storing chilled water, the soda tank being partially submerged in the separate tank, and wherein the soda tank and the separate tank are each provided with cooling coils for direct cooling.

12. The liquid supply system according to claim 10, wherein the soda machine further comprises an auxiliary $CO_2$ circulation system comprising an expansion tank, a pipe connecting the expansion tank to the soda tank via a pressure relief valve that opens when the pressure in the soda tank and the pipe exceeds a preset pressure and a further pipe connecting the expansion tank to the soda tank via a one-directional valve blocking a flow of the $CO_2$ gas and water or water droplets from the soda tank to the expansion tank.

13. The liquid supply system according to claim 10, wherein the $CO_2$ release mechanism further comprises a gap reducing mechanism adapted to reduce a backlash between components of the $CO_2$ release mechanism and the $CO_2$ container due to accumulated engineering tolerances of these components and/or due to changes in the mounting position of the $CO_2$ container when the $CO_2$ container is exchanged.

14. The liquid supply system according to claim 13, wherein the $CO_2$ release mechanism further comprises:
a lever mechanism for opening the $CO_2$ container against the closing force of a container closing valve;
an actuator with a movable actuator part adapted to move between an activated position and a non-activated position; and
the gap reducing mechanism further comprising:
a spring coupled between the lever mechanism and the movable actuator part and biasing the movable actuator part toward the non-activated position, and
at least one clamping element pivotably connected to the movable actuator part and being displaceable between a clamping position, in which it is in clamping engagement with the lever mechanism, and a release position, in which the lever mechanism may freely move relative to the movable actuator part, a movement of the movable actuator part from its activated position to its non-activated position displacing the at least one clamping element towards its release position.

15. The liquid supply system according to claim 1, comprising a liquid level sensor unit provided in a water tank, said water tank being made from a conductive material and being connected to ground, the liquid level sensor unit comprising:
a power supply providing a predetermined voltage;
a conductive sensor tip provided at a predetermined height over a bottom of the water tank, the sensor tip being electrically connected to the power supply via a resistor; and
a device for detecting a voltage at a predetermined point between the resistor and the sensor tip.

16. A faucet, in particular as a part of a water-based liquid supply system according to claim 1, said faucet comprising at least two internal conduits, the internal conduits being separated from each other.

17. The faucet according to claim 16, wherein one of the internal conduits is an inner conduit arranged within the other internal conduit, the inner conduit being further divided internally into at least two internal ducts which are separated from each other.

18. The faucet according to claim 17, wherein the inner conduit is thermally insulated in the faucet from an entry point to an outlet to prevent heat transfer between the liquid and the faucet.

19. The faucet according to claim 16, comprising a fixed faucet base and a swiveling spout, wherein the at least two internal conduits are arranged coaxially and have a circular cross-section at least in a region in which the swiveling spout is connected to the fixed faucet base.

20. The faucet according to claim 16, comprising a fixed faucet base and a swiveling spout, wherein for at least one of the internal conduits, a flexible pipe is inserted in the spout or part of it, the flexible pipe connecting the respective internal conduit in the swiveling spout with a pipe extending in the faucet base.

21. The faucet according to claim 16, comprising a selector device designed to select a water-based liquid from a predetermined number of different kinds of water-based liquids, each of these different kinds of water-based liquids being associated with a different predetermined indication, and wherein the faucet further comprises a display device adapted to display the specific predetermined indication associated with the kind of water-based liquid that is currently being selected, prepared or dispensed.

22. The faucet according to claim 21, comprising a selector device for selecting the desired type of liquid, wherein the selector device is adapted to be rotated around an axis in predefined steps synchronized with the display device.

23. The faucet according to claim 22, wherein the selector device is illuminated and comprises at least two optical sensor elements positioned at a predetermined location and at a predetermined angular distance from each other in order to detect light reflected by the selector device.

24. The faucet according to claim 16, further comprising:
a selector knob for selecting the desired kind of water-based liquid, the selector knob comprising an outer shell being adapted for rotation around an axis in predefined steps with respect to a fixed part, a reflecting element provided on one part, namely the outer shell or the fixed part, an illuminating element provided on the respective other part, namely the fixed part or the outer shell, and adapted to illuminate the reflecting element, and an optical sensor device provided on the respective other part, and adapted to detect the intensity of light reflected from the reflecting element so that a rotation of the outer shell by one step is detected by a change of the intensity of light reflected from the reflecting element.

25. A liquid level sensor, in particular as a part of a water-based liquid supply system according to claim 1, said liquid level sensor comprising at least one electrode powered by an electrical voltage supply, the liquid sensor being adapted to detect an electrically conductive liquid in a grounded tank when the liquid enters into contact with the sensor.

26. The liquid level sensor according to claim 25, comprising a resistor and an electrical circuit connecting the electrical voltage supply to the sensor via the resistor, so that a voltage drop over the resistor changes whenever a grounded liquid enters into contact with the sensor.

27. A UV sterilizing device, in particular as a part of a water-based liquid supply system according to claim 1, said UV sterilizing device being adapted to sterilize a liquid in a tank or flowing through a pipe by irradiating it with UV light.

28. The UV sterilizing device according to claim 27, the UV light sources being provided inside a tank or a pipe.

29. The UV sterilizing device according to claim 27, the UV light sources being provided outside a tank or a pipe, said tank or pipe being at least locally transparent.

30. A control and communication system, in particular as a part of a water-based liquid supply system according to claim 1, said control and communication system being adapted to control at least one smart device, in particular at least one smart kitchen appliance, the control and communication system being adapted to connect the at least one smart devices with communication capability, a hood, a cooker or the like, in such a manner that the smart device can communicate with a user and/or in case of at least two smart devices with each other using short distance communication technology for activating, programming, and controlling the system.

31. The control and communication system according to claim 30, wherein the communication and control system is adapted to be accessed by the user via a local, proprietary control panel and/or via a mobile device, and wherein the communication and control system is adapted to be accessed by the user directly and/or via a local hub and/or a local network and/or via cloud communication through the internet.

32. The control and communication system according to claim 30, comprising a local hub or a router adapted to allow the communication between each of the devices connected by the system through the local hub.

33. The control and communication system according to claim 32, wherein the local hub connects the system to a cloud for remote setup and communication, to provide predetermined services.

34. The control and communication system according to claim 30, wherein the control and communication system is a cloud communication system having an indoor hub connecting indoor smart devices and a virtual hub held in the cloud for managing communication between external smart devices located outdoor, the indoor hub, the indoor smart devices and the user.

35. The control and communication system unit according to claim 34, wherein the indoor hub is adapted to communicate with the virtual hub for providing the system with web server capabilities.

36. The faucet according to claim 24, wherein the reflecting element is a reflector ring or a reflector disk divided in n sectors of equal size and having alternatingly high and low reflectivity, n being a natural even number and each sector covering an circumferential angle of 360°/n, and wherein the sensor device comprises two sensor elements arranged in a circumferential di stance of 180°/n.

37. A soda machine as a part of a water-based liquid supply system for preparing and dispensing water-based liquids at a desired temperature and with at least one additive at a desired concentration on demand, said soda machine comprising:

a $CO_2$ container containing $CO_2$ gas at a $CO_2$ container pressure;

a soda tank connected to a water supply and to the $CO_2$ container, the connection between the $CO_2$ container and the soda tank being free of a pressure reducer;

a $CO_2$ release mechanism for releasing and injecting the $CO_2$ gas from the $CO_2$ container directly into the soda tank through a nozzle located in the soda tank; and a check valve installed in a line connecting the $CO_2$ container and the soda tank and preventing the $CO_2$ gas from flowing back from the soda tank to the $CO_2$ container, wherein the liquid supply system comprises:

at least one faucet having an outlet for dispensing the prepared water-based liquid, a water filter adapted to filter water from the water supply, at least one of a water boiler adapted to heat water from the water supply to a predetermined temperature or a water chiller adapted to cool water from the water supply to a predetermined temperature, an additive mixer adapted to mix at least one additive supplied from at least one additive container at a predetermined concentration to water from the water supply, wherein the at least one additive is different from the $CO_2$ gas, a piping system connecting the water supply, the faucet, the water filter, the soda machine, the additive mixer, and the at least one of the water boiler or the water chiller, and a communication and control system adapted to communicate with a user and to control the preparation and dispensing of the water-based liquid based on a communication with the user.

38. The soda machine according to claim 37, wherein the soda machine is adapted for preparing soda by mixing the $CO_2$ gas in a predetermined amount of water for delivering continually one or more cups of carbonated water mixed with at least one of plain water or other additives.

39. The soda machine according to claim 37, wherein an operating process for preparing soda or part of said operating process is an automatic operating process that is interruptible at any time and replaceable by manual commands.

40. The soda machine according to claim 37, further comprising a cooling system adapted to keep the soda tank cooled to a predetermined temperature or temperature range for storing and consumption at any time.

41. The soda machine according to claim 37, wherein the soda tank comprises an air trap at the top of the tank to limit the highest water level, wherein an upper water level and a lower water level may be detected by corresponding sensors, respectively, or alternatively be controlled by a software application controlling a water filling process by a timer and calculating whether the corresponding water lever has been reached based on an amount of soda consumed or water filled in, respectively.

42. The soda machine according to claim 37, wherein the soda machine is adapted to control a concentration of the $CO_2$ gas by a controller with or without a software application, controlling soda preparation parameters, an injection pattern of the injected $CO_2$ gas, a pressure held in the soda tank while injecting the $CO_2$ gas.

43. The soda machine according to claim 37, further comprising a pressure sensor in communication with the soda tank to limit the maximum pressure allowed in the tank and/or to influence the $CO_2$ injection amount and/or to influence the soda intensity and/or to detect low pressure and inject additional amount of $CO_2$ gas for keeping the required pressure in the tank and/or to detect after injection the need to replace the empty $CO_2$ container.

44. The soda machine according to claim 37, further comprising a Bluetooth and/or WIFI connection for remote controlling and operating and/or for communicating with other smart appliances and/or for providing cloud services.

45. The soda machine according to claim 37, further comprising a separate tank for storing chilled water, the soda tank being submerged partially in the separate tank, and wherein the soda tank and the separate tank are each provided with cooling coils for direct cooling.

46. The soda machine according to claim 37, further comprising a separate tank for storing chilled water, the separate tank having a connection for a water main line and wherein the soda machine is adapted to refill the water tank automatically whenever water flows out of the water tank.

47. The soda machine according to claim 37, further comprising a relief pipe with a controllable solenoid valve adapted to release the pressure from the soda tank when required.

48. The soda machine according to claim 47, wherein an inlet of the relief pipe is positioned in the soda tank at a predetermined height below the top level to create an air trap at the top of the tank, preventing the water from occupying the full volume of the tank and securing free space for the $CO_2$ gas injected into the tank.

49. The soda machine according to claim 37, further comprising an auxiliary $CO_2$ circulation system for keeping undissolved $CO_2$ injected to the soda tank, and returning it back to the soda tank, when the pressure in the soda tank drops, for maintaining a desired controlled pressure in the soda tank, and for preventing the need to handle water drops flushed together with the $CO_2$ gas exhausted;
wherein the auxiliary $CO_2$ circulation system comprises a pipe connecting the expansion tank to the soda tank via a pressure relief valve that opens when the pressure in the soda tank; and
wherein the pipe exceeds a preset pressure and a further pipe connecting the expansion tank to the soda tank via a one-directional valve balancing the pressure between the expansion tank and the soda tank.

50. The soda machine according to claim 37, further comprising a $CO_2$ container magazine for holding a plurality of $CO_2$ containers.

51. The soda machine according to claim 50, wherein the soda machine is adapted to monitor the current number of full $CO_2$ containers in the magazine and to output a warning when this number drops below a preset threshold.

52. The soda machine according to claim 37, wherein the $CO_2$ release mechanism further comprises a gap reducing mechanism adapted to reduce a backlash between components of the $CO_2$ release mechanism and the $CO_2$ container due to accumulated engineering tolerances of these components and/or due to changes in the mounting position of the $CO_2$ container when the $CO_2$ container is exchanged.

53. The soda machine according to claim 52, wherein the $CO_2$ release mechanism further comprises:
a lever mechanism for opening the $CO_2$ container against the closing force of a container closing valve; and
an actuator with a movable actuator part adapted to move between an activated position and a non-activated position,
the gap reducing mechanism further comprising:
a spring coupled between the lever mechanism and the movable actuator part and biasing the movable actuator part toward the non-activated position, and
at least one clamping element pivotably connected to the movable actuator part and being displaceable between a clamping position, in which it is in clamping engagement with the lever mechanism, and a release position, in which the lever mechanism may freely move relative to the movable actuator part, a movement of the movable actuator part from its activated position to its non-activated position displacing the at least one clamping element towards its release position.

* * * * *

UNITED STATES PATENT AND TRADEMARK OFFICE
CERTIFICATE OF CORRECTION

PATENT NO. : 11,772,952 B2
APPLICATION NO. : 16/291110
DATED : October 3, 2023
INVENTOR(S) : Yuval-Yoni Dahan and Abraham Dahan It is certified that error appears in the above-identified patent and that said Letters Patent is hereby corrected as shown below:

In the Claims

In Claim 4, Column 36, Line 36, "the consumption of at least one consumable part of the" should read -- a consumption of at least one consumable part of the --

In Claim 6, Column 36, Line 49, "additionally filled into the tank and the resulting temperature" should read --additionally filled into the tank and a resulting temperature --

In Claim 8, Column 36, Line 62, "a selector knob for selecting the desired kind of water-" should read -- a selector knob for selecting a desired kind of water- --

In Claim 8, Column 37, Line 5, "part, and adapted to detect the intensity of light" should read -- part, and adapted to detect an intensity of light --

In Claim 13, Column 37, Line 52, "these components and/or due to changes in the mounting" should read -- these components and/or due to changes in a mounting --

In Claim 14, Column 37, Line 58, "the closing force of a container closing valve;" should read -- a closing force of a container closing valve; --

In Claim 24, Column 39, Line 9, "part, and adapted to detect the intensity of light" should read -- part, and adapted to detect an intensity of light --

In Claim 28, Column 39, Line 31, "The UV sterilizing device according to claim 27, the" should read -- The UV sterilizing device according to claim 27, --

In Claim 29, Column 39, Line 33, "The UV sterilizing device according to claim 27, the" should read -- The UV sterilizing device according to claim 27, --

Signed and Sealed this
Ninth Day of January, 2024

Katherine Kelly Vidal
*Director of the United States Patent and Trademark Office*

CERTIFICATE OF CORRECTION (continued)
U.S. Pat. No. 11,772,952 B2

In Claim 41, Column 41, Line 7 "calculating whether the corresponding water lever has been" should read -- calculating whether the corresponding water level has been --

In Claim 43, Column 41, Line 20 "influence the soda intensity and/or to detect low pressure and" should read -- influence a soda intensity and/or to detect low pressure and --

In Claim 43, Column 41, Line 21 "inject additional amount of CO2 gas for keeping the required" should read -- inject additional amount of CO2 gas for keeping a required --

In Claim 43, Column 41, Line 22 "pressure in the tank and/or to detect after injection the need" should read -- pressure in the tank and/or to detect after injection a need --

In Claim 48, Column 41, Line 44 "predetermined height below the top level to create an air trap" should read -- predetermined height below a top level to create an air trap --

In Claim 48, Column 41, Line 45 "at the top of the tank, preventing the water from occupying" should read -- at a top of the tank, preventing the water from occupying --

In Claim 48, Column 41, Line 46 "the full volume of the tank and securing free space for the" should read -- a full volume of the tank and securing free space for the --

In Claim 49, Column 42, Line 4 "soda tank, and for preventing the need to handle water drops" should read -- a soda tank, and for preventing a need to handle water drops --

In Claim 49, Column 42, Line 7 "pipe connecting the expansion tank to the soda tank via" should read -- pipe connecting an expansion tank to the soda tank via --

In Claim 51, Column 42, Line 18 "soda machine is adapted to monitor the current number of" should read -- soda machine is adapted to monitor a current number of --

In Claim 52, Column 42, Line 26 "nents and/or due to changes in the mounting position of the" should read -- nents and/or due to changes in a mounting position of the --